US010071142B2

(12) United States Patent
Garrido et al.

(10) Patent No.: US 10,071,142 B2
(45) Date of Patent: Sep. 11, 2018

(54) ENZYMES AND METHODS FOR CLEAVING N-GLYCANS FROM GLYCOPROTEINS

(71) Applicant: The Regents of the University of California, Oakland, CA (US)

(72) Inventors: Daniel Garrido, Santiago (CL); J. Bruce German, Davis, CA (US); Carlito B. Lebrilla, Davis, CA (US); David A. Mills, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/079,949

(22) Filed: Mar. 24, 2016

(65) Prior Publication Data
US 2016/0287680 A1   Oct. 6, 2016

Related U.S. Application Data

(63) Continuation of application No. 14/378,190, filed as application No. PCT/US2013/026183 on Feb. 14, 2013, now Pat. No. 9,327,016.

(60) Provisional application No. 61/598,593, filed on Feb. 14, 2012.

(51) Int. Cl.
| C12N 9/24 | (2006.01) |
| C12P 19/04 | (2006.01) |
| A61K 38/01 | (2006.01) |
| A61K 38/47 | (2006.01) |
| A23L 2/52 | (2006.01) |
| A61K 31/715 | (2006.01) |
| A61K 35/741 | (2015.01) |
| A23C 9/12 | (2006.01) |
| C12P 21/00 | (2006.01) |
| A23L 33/195 | (2016.01) |
| A61K 38/40 | (2006.01) |
| C07K 14/79 | (2006.01) |
| A61K 38/00 | (2006.01) |

(52) U.S. Cl.
CPC ............ *A61K 38/47* (2013.01); *A23C 9/1216* (2013.01); *A23L 2/52* (2013.01); *A23L 33/195* (2016.08); *A61K 31/715* (2013.01); *A61K 35/741* (2013.01); *A61K 38/40* (2013.01); *C07K 14/79* (2013.01); *C12N 9/2402* (2013.01); *C12N 9/2497* (2013.01); *C12P 19/04* (2013.01); *C12P 21/005* (2013.01); *A61K 38/00* (2013.01); *C12Y 302/01096* (2013.01); *Y02P 20/52* (2015.11)

(58) Field of Classification Search
CPC .... A61K 31/715; A61K 38/47; A61K 35/741; C07K 14/00; C12N 9/2497; C12N 24/02; A23C 9/1216
USPC ........................................ 435/183, 6, 252.3
See application file for complete search history.

(56) References Cited

U.S. PATENT DOCUMENTS

| 6,815,191 B1 | 11/2004 | Kobayashi et al. |
| 2011/0053215 A1 | 3/2011 | Koutsioulis et al. |
| 2011/0287559 A1 | 11/2011 | Zangmeister et al. |
| 2015/0110771 A1 | 4/2015 | Garrido et al. |

FOREIGN PATENT DOCUMENTS

WO   2011127322   10/2011

OTHER PUBLICATIONS

Abbott et al., "*Streptococcus pneumoniae* endohexosaminidase D, structural and mechanistic insight into substrate-assisted catalysis in family 85 glycoside hydrolases", Journal of Biological Chemistry, vol. 284, No. 17, Apr. 24, 2009, pp. 11676-11689.
Bohle et al., "An endo-β-N-acetylglucosaminidase from Enterococcus faecalis V583 responsible for the hydrolysis of high-mannose and hybrid-type N-linked glycans", FEMS Microbiology Letters, vol. 325, No. 2, Dec. 4, 2011, pp. 123-129.
Collin et al., "A novel secreted endoglycosidase from Enterococcus faecalis with activity on human immunoglobulin G and ribonuclease B", Journal of Biological Chemistry, American Society for Biochemistry and Molecular Biology, US, val. 279, No. 21, May 21, 2004, pp. 22558-22570.
Fukuda et al., "UniProt Database", Accession No. E8MUK6_BIFL 1, 2011.
Garrido, et al., "Endo-(beta)-N-acetylglucosaminidases from infant gut-associated bifidobacteria release complex N-glycans from human milk glycoproteins"; Mol. Cell. Proteomics; 11(9):775-785 (2012) ePub Jun. 27, 2012.
Sela et al., "UniProt Database", Accession No. B7GPC7 BIFLS, 2009.
International Search Report and Written Opinion from PCT/US2013/026183, dated Jul. 22, 2013.
Fukuda et al, "Bifidobacteria can protect from enteropathogenic infection through production of acetate," Nature 469, Jan. 27, 2011, 543-547.
Sela et al., "The genome sequence of *Bifidobacterium longum* subsp. *infantis* reveals adaptations for milk utilization within the infant microbiome," PNAS vol. 105, No. 48, Dec. 2, 2008, 18964-18969.

(Continued)

Primary Examiner — Maryam Monshipouri
(74) Attorney, Agent, or Firm — Kilpatrick Townsend & Stockton LLP

(57) ABSTRACT

Provided herein are deglycosylating enzymes that remove a broad range of N-glycans from N-glycosylated proteins. Further provided are methods of recombinantly producing and expressing the deglycosylating enzymes. The presently described deglycosylating enzymes can be used to produce free glycans for characterization, and for prebiotic and immunostimulatory uses. In addition, the presently described deglycosylating enzymes can be used to produce deglycosylated proteins for characterization, to improve digestion, and to reduce immunogenicity.

11 Claims, 14 Drawing Sheets
Specification includes a Sequence Listing.

(56) References Cited

OTHER PUBLICATIONS

Pearson, "An Introduction to Sequence Similarity ("Homology") Searching," Curr Protoc Bioinformatics. Jun. 2013, 9 pages.
Davies et al., "Sorting the diverse: the sequence-based classifications of carbohydrate-active enzymes." Biochem J 30 (2008): 26-32.

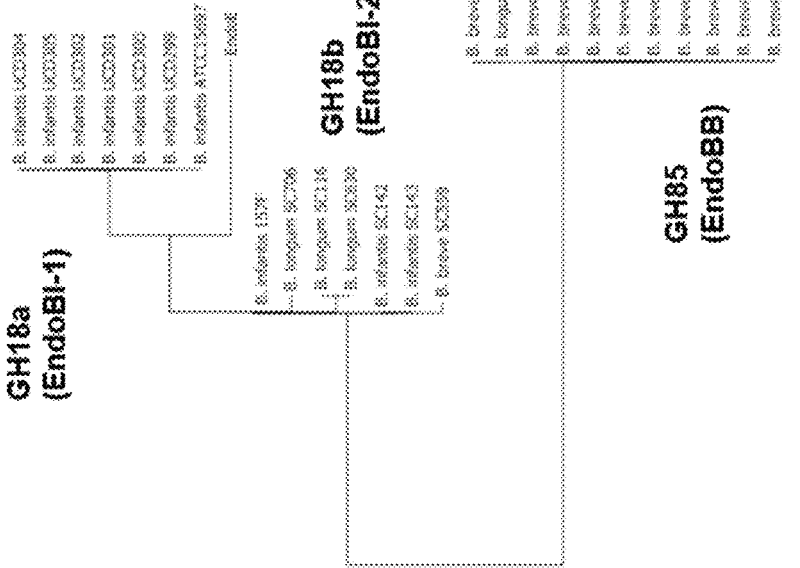
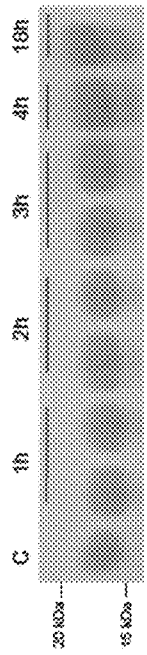
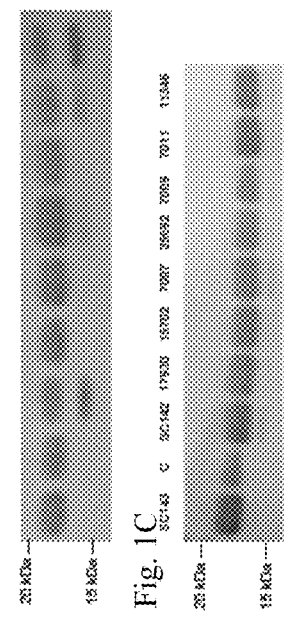
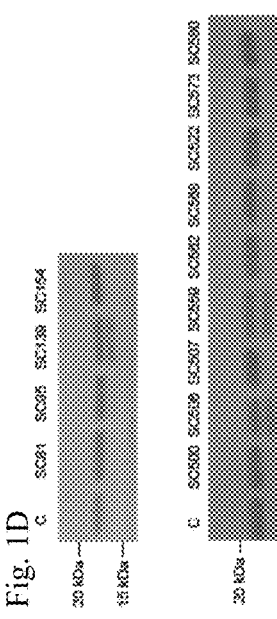
Fig. 1A
Fig. 1B
Fig. 1C
Fig. 1D
Fig. 1E

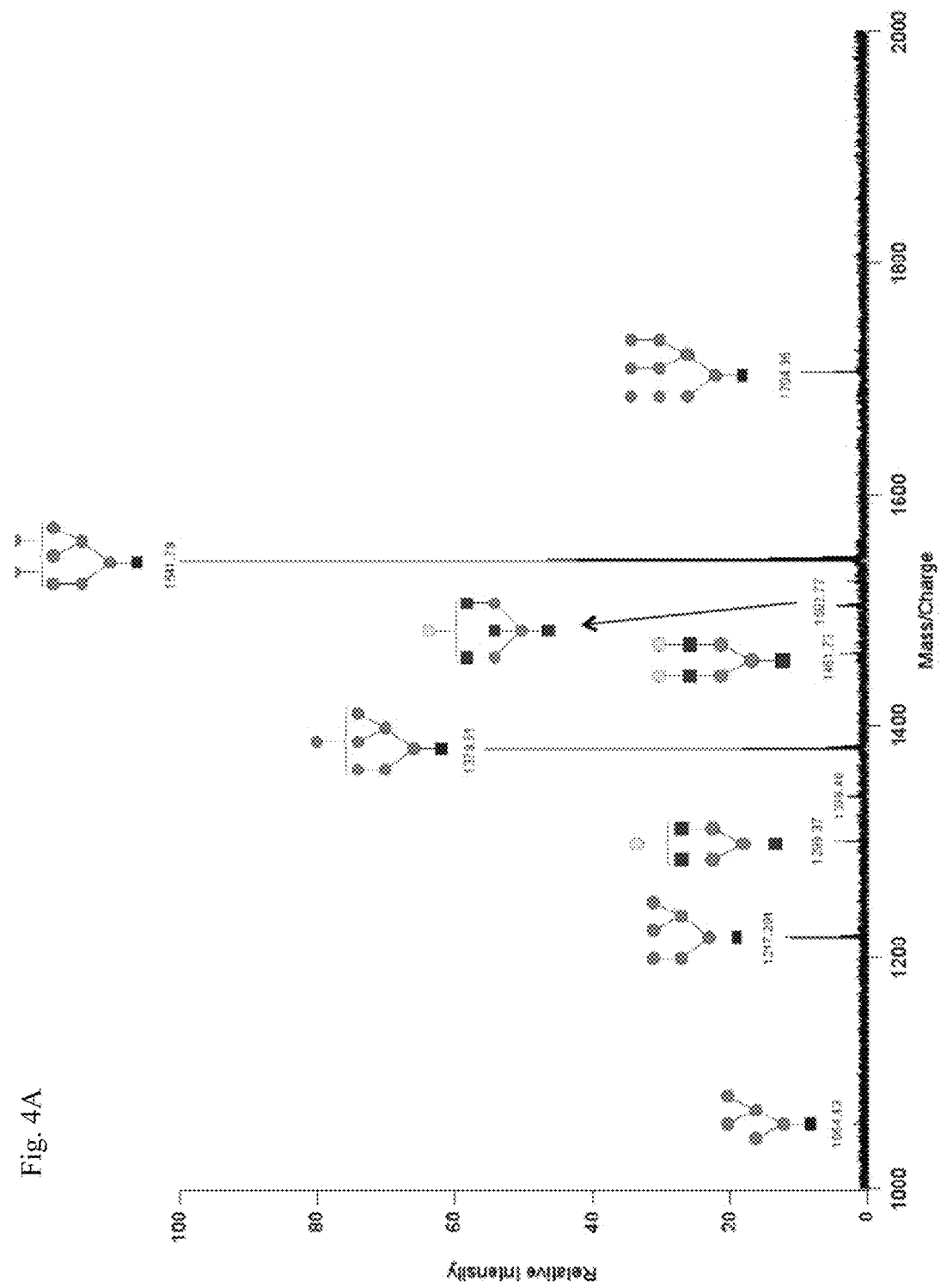

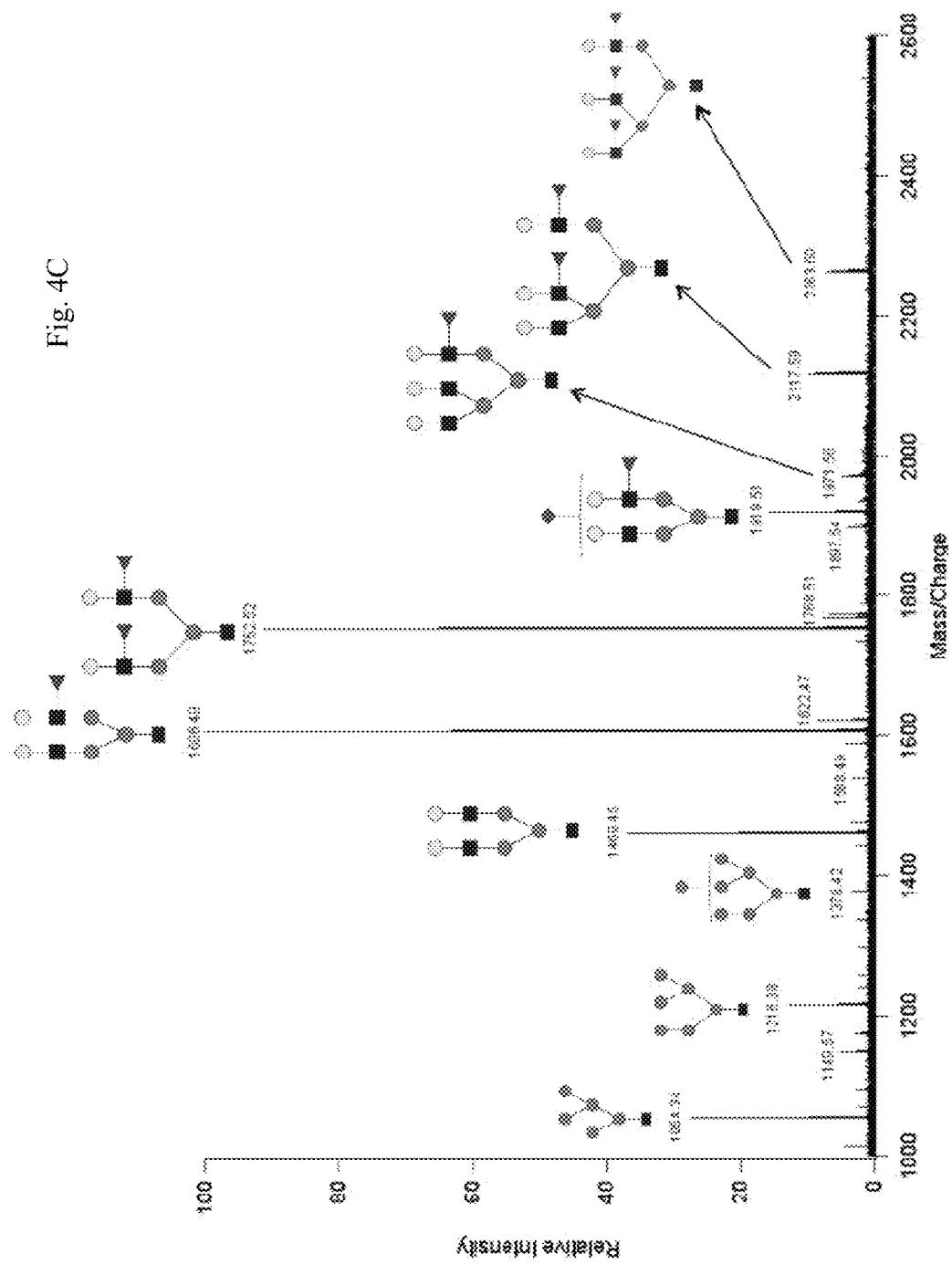

ENZYMES AND METHODS FOR CLEAVING N-GLYCANS FROM GLYCOPROTEINS

CROSS-REFERENCE TO RELATED PATENT APPLICATIONS

The present patent application is a continuation of U.S. patent application Ser. No. 14/378,190, filed on Aug. 12, 2014, which is a US National Stage entry of International Application No. PCT/US2013/026183, filed Feb. 14, 2013, which claims benefit of priority to U.S. Provisional Application No. 61/598,593, filed Feb. 14, 2012, of which the disclosure of each application is incorporated herein in its entirety.

BACKGROUND OF THE INVENTION

The presence of certain species of *Bifidobacterium* is commonly observed in breast-fed infants (Roger & McCartney, *Microbiology* 156:3317-3328 (2010)), and a bifidobacterial-dominant micobiota is thought to be associated with beneficial health effects (Le Huerou-Luron et al., *Nutr Res Rev* 23:23-36 (2010); Conroy et al., *Curr Opin Allergy Clin Immunol* 9:197-201 (2009)). This enrichment has been in part explained by the ability of bifidobacteria to degrade and utilize human milk oligosaccharides (HMO) as a carbon source (Ward et al., *Mol Nutr Food Res* 51:1398-1405 (2007)). HMOs are complex free structures that escape digestion by intestinal enzymes (Kunz et al., *Annu Rev Nutr* 20:699-722 (2000)). Among infant-associated *bifidobacteria*, *B. longum* subsp. *infantis* (*B. infantis*) ATCC 15697 has been studied for its ability to consume HMO in vitro and in vivo (LoCascio et al., *J Agric Food Chem* 55:8914-8919 (2007); Marcobal et al., *Cell Host Microbe* 10:507-514 (2011); Sela et al., *Proc Natl Acad Sci USA* 105:18964-18969 (2008); Sela et al., *J Biol Chem* 286:11909-11918 (2011); Garrido et al., *PLoS One* 6:e17315 (2011); Sela et al., *Applied and Environmental Microbiology* (2011)).

A great variability in protein types and abundances is found in the breast milk of different mothers at different stages of lactation (Mitoulas et al., *Br J Nutr* 88:29-37 (2002)). Milk proteins are readily utilized by the infant (Prentice et al., *Acta Paediatr Scand* 76:592-598 (1987)), and can play critical functions in protection of the newborn. For example, human lactoferrin (hLF) is one of the most abundant proteins in human milk, and hLF or its derived peptides display broad antimicrobial and anti-inflammatory effects, among several biological activities (Gonzalez-Chavez et al., *Int J Antimicrob Agents* 33:301 e301-308 (2009)).

Many human milk proteins, as well as virtually all secreted proteins in eukaryotes, are glycosylated (Froehlich et al., *J Agric Food Chem* 58:6440-6448 (2010)). While milk caseins are O-linked glycosylated, lactoferrin and immunoglobulins contain N-linked glycans (Picariello et al., *Proteomics* 8:3833-3847 (2008)). Asparagine-linked glycosylation is the most common post-translational modification of eukaryotic proteins (Apweiler et al., *Biochim Biophys Acta* 1473:4-8 (1999)). N-linked glycosylation (N-glycosylation) plays a role in folding, secretion, and resistance to proteolysis (Weber et al., *J Biol Chem* 279:34589-34594 (2004); Roth et al., *Mol Cells* 30:497-506 (2010)), protein function, such as bacterial recognition (Mathias & Corthesy, *J Biol Chem* 286:17239-17247 (2011)), intracellular signaling (Sun et al., *J Biol Chem* 281:11144-11151 (2006)) and antigen binding and presentation (Ryan et al., *J Exp Med* 208:1041-1053 (2011)).

Certain microorganisms, mostly pathogens, have also acquired the ability to release N-glycans from glycoproteins, e.g., for use as a carbon source (Renzi et al., *PLoS Pathog* 7:e1002118 (2011)) or to alter the biological function of certain glycoproteins such as immunoglobulins (Collin et al., *Proc Natl Acad Sci USA* 105:4265-4270 (2008)). Bacterial Endo-β-N-acetylglucosaminidases (EC 3.2.1.96; endoglycosidases) are enzymes that cleave the N—N'-diacetyl chitobiose of the core pentasaccharide Man$_3$GlcNAc$_2$ found in all N-glycans (Varki, *Essentials of glycobiology* (Cold Spring Harbor Laboratory Press, Cold Spring Harbor, N.Y.) 2nd Ed pp xxix, 784 p. (2009)). These enzymes belong to glycosyl hydrolase families GH18 or GH85. Prominent examples are EndoH from *Streptomyces plicatus* (Trimble & Maley, *Biochem Biophys Res Commun* 78:935-944 (1977)), EndoE from *Enterococcus faecalis* (Collin & Fischetti, *J Biol Chem* 279:22558-22570 (2004)) and EndoS from *Streptococcus pyogenes* (Allhorn et al., *PLoS One* 3:e1413 (2008)), while EndoD from *Streptococcus pneumoniae* (Muramatsu et al., *J Biochem* 129:923-928 (2001)) is a member of GH85. Previously characterized GH18 and GH85 endoglycosidases are of limited substrate specificity, to either high mannose or complex N-glycans and some require additional exoglycosidases for complete cleavage of the N-glycan.

Provided herein are deglycosylating enzymes (endoglycosidases) that cleave N-glycans from glycoproteins, but with a broad substrate range, able to cleave high mannose, hybrid and complex N-glycans from N-glycoproteins. The deglycosylating enzymes are active on N-glycans with terminal fucosylation and/or sialylation, and/or core fucosylation, and in a broad range of conditions.

BRIEF SUMMARY OF THE INVENTION

Provided herein are deglycosylating enzymes with broad substrate range for N-glycans (see, e.g., Section III below). Further provided are free N-glycans released by the enzymes, and deglycosylated proteins produced by the enzymes. Also included are methods for generating and using the presently described deglycosylating enzymes, free N-glycans, and deglycosylated proteins.

In some embodiments, provided is a recombinant polypeptide, e.g., a deglycosylating enzyme as disclosed in Section III, wherein the polypeptide can cleave high mannose, complex, and hybrid N-glycans from a glycoprotein. In some embodiments, the polypeptide lacks a transmembrane domain that spans a cell membrane. In some embodiments, the polypeptide comprises a sequence of GLDIDME (SEQ ID NO:1). In some embodiments, the polypeptide comprises a sequence having at least 90% identity to any one of SEQ ID NOs:4, 5, and 7-20 (e.g., 94, 95, 96, 97, 98, 99, or 100% identity). In some embodiments, the N-glycan includes core fucosylation, terminal fucosylation, or terminal sialylation. In some embodiments, the polypeptide is active (detectably cleaves N-glycan from a glycoprotein) at a pH of about 4-8, e.g., 4.5-7.5, or 5-7. In some embodiments, the polypeptide is active after 5 minute treatment at 95 C.

Also provided is a recombinant polypeptide, e.g., a deglycosylating enzyme as disclosed in Section III, wherein the polypeptide can cleave high mannose, complex, and hybrid N-glycans from a glycoprotein, and wherein the polypeptide is expressed in a cell, e.g., as a transmembrane protein at the cell surface. In some embodiments, the polypeptide comprises a sequence of GLDIDME (SEQ ID NO:1). In some embodiments, the polypeptide comprises a sequence having at least 90% identity (e.g., 94, 95, 96, 97, 98, 99, or 100% identity) to the full length mature sequence of EndoBI-1 or EndoBI-2. Accordingly, further provided are cells, e.g., recombinant cells, that express the polypeptide (deglycosylating enzyme) comprising a sequence of GLDIDME (SEQ ID NO:1), wherein the polypeptide can cleave high mannose, complex, and hybrid N-glycans from a glycoprotein. In some embodiments, the cells are bacterial cells, e.g., food grade bacteria.

In some embodiments, the polypeptide or deglycosylating enzyme-expressing cell is included in a pharmaceutical composition further comprising a pharmaceutically acceptable excipient, e.g., for oral administration. In some embodiments, the polypeptide is included in a food product, beverage, or consumer product (e.g., a lotion or ointment for dermal administration). In some embodiments, the food product or beverage is used to increase efficiency of protein digestion and/or induce satiety and/or reduce allergenic response to a glycoprotein in an individual.

Also provided are methods of deglycosylating a glycoprotein comprising a high mannose, complex, or hybrid N-glycan, the method comprising contacting the glycoprotein with a polypeptide (e.g., a deglycosylating enzyme as disclosed in Section III), thereby deglycosylating the glycoprotein and generating deglycosylated protein and free glycan. In some embodiments, the contacting is in vitro, e.g., in a laboratory or otherwise not in the body of a host organism. In some embodiments, the method further comprises separating the deglycosylated protein, e.g., from the free glycan and polypeptide (deglycosylating enzyme). In some embodiments, the method further comprises separating the free glycan, e.g., from the deglycosylated protein and the polypeptide (deglycosylating enzyme).

Thus in some embodiments, provided are methods of producing free glycan comprising contacting a glycoprotein comprising a high mannose, complex, or hybrid N-glycan with a polypeptide as described herein (e.g., a deglycosylating enzyme as disclosed in Section III), thereby deglycosylating the glycoprotein and generating deglycosylated protein and free glycan, and separating the free glycan from the deglycosylated protein and polypeptide. In some embodiments, the contacting is in vitro. In some embodiments, the glycoprotein is a milk glycoprotein (e.g., from a human, bovine, or goat), an egg glycoprotein, or a plant glycoprotein. In some embodiments, the polypeptide lacks a transmembrane domain that spans a cell membrane. In some embodiments, the polypeptide is a transmembrane protein in a cell. In some embodiments, the method further comprises characterizing the free glycan (e.g., using mass spectrometry, determining size, determining saccharide composition, etc.). In some embodiments, provided is a composition comprising free glycans (N-glycans) produced by contacting a glycoprotein comprising a high mannose, complex, or hybrid N-glycan with a polypeptide comprising a sequence of GLDIDME (SEQ ID NO:1), wherein the polypeptide can cleave high mannose, complex, and hybrid N-glycans from a glycoprotein. In some embodiments the composition comprises at least two or three types of N-glycan. In some embodiments, the free N-glycan has a core structure of Man$_3$GlcNAc (i.e., one core GlcNAc instead of two). In some embodiments, the free N-glycan includes core fucosylation, terminal fucosylation, or terminal sialylation. In some embodiments, the free glycan is included in a food product, beverage, pharmaceutical composition or consumer product. In some embodiments, the food product or beverage is used to stimulate growth of beneficial bacteria (e.g., *Bifidobacteria*) in a human or animal, or improve the immune response of an individual to a given glycoprotein or free glycan.

In some embodiments, provided are methods of producing deglycosylated protein comprising contacting a glycoprotein comprising a high mannose complex, or hybrid N-glycan with a polypeptide as described herein (e.g., a deglycosylating enzyme as disclosed in Section III), thereby deglycosylating the glycoprotein and generating deglycosylated protein and free glycan, and separating the deglycosylated protein from the free glycan and polypeptide. In some embodiments, the contacting is in vitro. In some embodiments, the polypeptide lacks a transmembrane domain that spans a cell membrane. In some embodiments, the polypeptide is a transmembrane protein in a cell. In some embodiments, the glycoprotein is a milk glycoprotein (e.g., from a human, bovine, or goat), an egg glycoprotein, or a plant glycoprotein. In some embodiments, the method further comprises characterizing the deglycosylated protein (e.g., determining size, sequence, charge, etc.). In some embodiments, provided is a composition comprising deglycosylated protein produced by contacting a glycoprotein comprising a high mannose complex, or hybrid N-glycan with a polypeptide comprising a sequence of GLDIDME (SEQ ID NO:1), wherein the polypeptide can cleave high mannose, complex, and hybrid N-glycans from a glycoprotein. In some embodiments, the deglycosylated protein retains a GlcNAc group at a previously glycosylated site. In some embodiments, the deglycosylated protein is included in a food product, beverage, or consumer product. In some embodiments, the food product or beverage is used to increase efficiency of protein digestion and/or induce satiety and/or reduce allergenic response to a glycoprotein in an individual.

Further provided are methods of recombinantly producing a polypeptide (e.g., a deglycosylating enzyme as disclosed in Section III), wherein said polypeptide comprises a sequence of: GLDIDME (SEQ ID NO:1) and can cleave high mannose, complex, and hybrid N-glycans from a glycoprotein, comprising culturing a cell comprising a recombinant polynucleotide encoding the polypeptide under conditions appropriate for expression of the polypeptide, thereby recombinantly producing the polypeptide. In some embodiments, the polypeptide lacks a transmembrane domain spanning a cell membrane. In some embodiments, the method further comprises isolating the polypeptide (e.g., separating the protein from other cellular components). In some embodiments, the polypeptide is a transmembrane protein in a cell.

Also provided is a composition comprising (i) a recombinant polypeptide comprising a sequence of: GLDIDME (SEQ ID NO:1), wherein said polypeptide can cleave high mannose, complex, and hybrid N-glycans from a glycoprotein (e.g., a deglycosylating enzyme as disclosed in Section III); and (ii) a glycoprotein, wherein the glycoprotein comprises a high mannose, complex, or hybrid N-glycan. In some embodiments, the glycoprotein is a milk glycoprotein (e.g., from a human, bovine, or goat), an egg glycoprotein, or a plant glycoprotein. In some embodiments, the polypeptide lacks a transmembrane domain spanning a cell membrane. In some embodiments, the polypeptide is a transmembrane protein in a cell.

Further provided are recombinant polypeptides derived from the presently disclosed deglycosylating enzymes with manipulated properties. For example, such manipulated-function recombinant polypeptides can include less than all of the activities of the presently disclosed deglycosylating enzymes, or that add an activity (e.g., binding to a separation moiety, etc.). A specific example of manipulated function recombinant polypeptides with fewer activities include polypeptides manipulated to have the same of similar ability to bind glycans and glycoprotein as a deglycosylating enzyme described herein, but lacking significant deglycosylation activity. Such polypeptides act as "lectins," i.e., proteins that bind glycans and carbohydrate moieties, but do not cleave. Such polypeptides can be designed by manipulating the active site conserved residues, e.g., within SEQ ID NOs:1 and 2. The example of EndoBI-1 D184N protein is shown, e.g., in Example 4. Such lectin-like, manipulated-function recombinant polypeptides can be used for separating glycoproteins, e.g., for subsequent characterization or deglycosylation.

BRIEF DESCRIPTION OF THE DRAWINGS

FIG. 1A-1E: Endoglycosidase activity in *Bifidobacterium* isolates. A: Time deglycosylation of RNAseB by *B. infantis* ATCC 15697. Overnight incubation with RNAseB was performed with other isolates of *B. longum* (B), *B. infantis* (C) or *B. breve* (D). E: Phylogenetic representation of endoglycosidase sequences found in bifidobacterial isolates.

FIG. 4A-4C: MALDI of free glycans released from (A) bLF, (B) hLF, and (C) IgA upon exposure to EndoBI-1.

DETAILED DESCRIPTION OF THE INVENTION

I. Introduction

Figure 2:
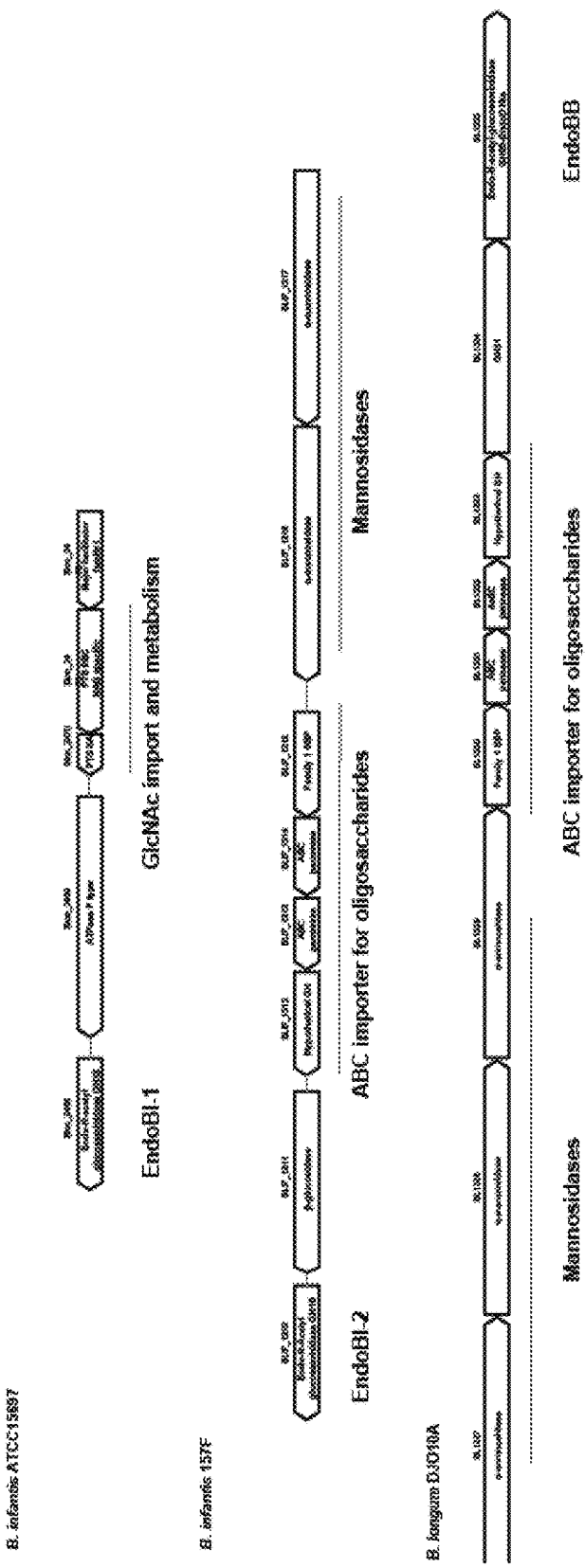
FIG. 2: Representation of gene landscapes for endoglycosidases found in organisms listed in the figure. IMG was used to obtain gene coordinates. GH: glycosyl hydrolase; SBP: solute-binding protein; PTS: phosphotransferase system.

The presently disclosed deglycosylating enzymes have a number of useful properties. In contrast to known deglycosylating enzymes, the present deglycosylating enzymes have at least the following benefits:
Promiscous cleavage of N-glycans, including high mannose, complex, and hybrid N-glycans, and those including fucosylation and/or sialylation;
Heat stability, which is advantageous for large-scale production and laboratory applications;
*Bifidobacteria*, which express the present deglycosylating enzymes at the cell surface, are considered food grade, or generally recognized as safe (GRAS), thus easing any regulatory hurdles for use in food or consumer products. The presently disclosed deglycosylating enzymes can also be expressed (e.g., heterologously) in other food grade bacteria.

Exemplary applications of the present deglycosylating enzymes:
Inclusion in food products (either as a polypeptide or as a cellular transmembrane protein), e.g.:
    To increase digestibility of glycoproteins, such as those found in milk;
    To stimulate growth of beneficial gut bacteria, e.g., in infants;
    To reduce allergenic response to food glycoproteins, e.g., in milk, nuts, soy, etc.;
    To induce satiety, e.g., for weight loss or maintenance.
Inclusion in pharmaceutical products, e.g.:
    To reduce allergenic potential and improve activity of therapeutic glycoproteins;
    To improve immune response to free glycans.
Analytical applications, e.g., high-throughput proteomics and glycoproteomics.
Production of deglycosylated proteins for, e.g.:
    Use in a food or consumer product with reduced allergenic potential;
    Use in a pharmaceutical composition with reduced allergic potential and more predictable chemical properties;
    Use in a food product with increased digestibility;
    Use for protein characterization and proteomic studies.
Production of free glycans for, e.g.:
    Use in a food product, e.g., as a prebiotic to stimulate growth of beneficial gut bacteria;
    Use in a pharmaceutical composition, e.g., for immune stimulation or pathogen protection;
    Use for glycan characterization and glycoproteomic studies.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The term "N-glycan" refers to an oligosaccharide comprising a core pentasaccharide $Man_3GlcNAc_2$. The N-glycan can be attached to a protein (glycoprotein) via the nitrogen of an asparagine (or occasionally arginine) residue, or free in solution. In the context of the present disclosure, the term "glycan" refers to an N-glycan unless otherwise specified. The terms "free glycan," "free N-glycan," and "oligosaccharide" refer to a glycan that is not covalently bound to a protein. A useful reference for glycan, glycoprotein, and oligosaccharide nomenclature can be found at the website chem.qmul.ac.uk/iupac/misc/glycp.html.

Unless specified, the term "deglycosylating enzyme" refers to the presently disclosed endoglycosidases with broad substrate range, as well as enzymes with more limited substrate specificities. The term "deglycosylating" generally refers to removing N-glycans from a protein. The term "deglycosylated protein" or "deglycosylated polypeptide" refers to a polypeptide that was at one point glycosylated (N-glycosylated), but has been exposed to a deglycosylating enzyme under appropriate conditions to reduce the number of or completely eliminate attached glycans.

The term "lacks a transmembrane domain that spans a cell membrane," with reference to a protein, indicates that the protein does not span a cell membrane as it would in its native state. The protein may include a domain with the characteristics of a transmembrane domain (e.g., hydrophobic residues).

The terms "isolating," "separating," and "purifying" are not intended to be absolute terms, but refer to separation of a polynucleotide, protein, glycan, cell, or other component from other materials in a sample, thereby substantially enriching the component. For example, in the context of a deglycosylation reaction, isolating the free glycans would entail separating the free glycans from the deglycosylated protein and the deglycosylating enzyme, e.g., using size or affinity based methods, or other methods familiar in the art.

The term "characterizing" can refer to determination of any characteristic of a polynucleotide, protein, glycan, cell, or other component. For example, characterizing a protein could entail determining the sequence, size, or function of the protein. Characterizing a glycan could entail determining, e.g., size or saccharide composition of the glycan using known methods, e.g., mass spectrometry.

The term "*Bifidobacteria*" and its synonyms refer to a genus of anaerobic bacteria having beneficial properties for humans. *Bifidobacteria* is one of the major strains of bacteria that make up the gut flora, the bacteria that reside in the gastrointestinal tract and have health benefits for their hosts. See, e.g., Guarner F and Malagelada J R. *Lancet* (2003) 361, 512-519, for a further description of *Bifidobacteria* in the normal gut flora.

A "prebiotic" or "prebiotic nutrient" is generally a non-digestible food ingredient that beneficially affects a host when ingested by selectively stimulating the growth and/or the activity of one or a limited number of bacteria in the gastrointestinal tract. As used herein, the term "prebiotic" refers to the above described non-digestible food ingredients in their non-naturally occurring states, e.g., after purification, chemical or enzymatic synthesis as opposed to, for instance, in whole human milk.

A "probiotic" refers to live microorganisms that when administered in adequate amounts confer a health benefit on the host.

A polynucleotide or polypeptide sequence is "heterologous to" an organism or a second sequence if it originates from a different species, or, if from the same species, it is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Similarly, a heterologous expression cassette includes sequence(s) that are from a different species than the cell into which the expression cassette is introduced, or if from the same species, is genetically modified.

"Recombinant" refers to a genetically modified polynucleotide, polypeptide, cell, tissue, or organism. When used with reference, e.g., to a cell, nucleic acid, protein, or vector, the term indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. For example, a recombinant polynucleotide (or a copy or complement of a recombinant polynucleotide) is one that has been manipulated to be different from its natural form. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). A recombinant expression cassette (or expression vector) typically comprises polynucleotides combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide).

The terms "nucleic acid," "oligonucleotide," "polynucleotide," and like terms typically refer to polymers of deoxyribonucleotides or ribonucleotides in either single- or double-stranded form, and complements thereof. The term "nucleotide" typically refers to a monomer. The terms encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "gene" refers to a segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene (e.g., promoters, enhancers, etc.). A "gene product" can refer to either the mRNA or protein expressed from a particular gene.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, *Molecular Cloning: A Laboratory Manual,* 18.1-18.88.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

An expression vector refers to a nucleic acid that includes a coding sequence and sequences necessary for expression of the coding sequence. The expression vector can be viral or non-viral. A "plasmid" is a non-viral expression vector, e.g., a nucleic acid molecule that encodes for genes and/or regulatory elements necessary for the expression of genes. A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Conservatively modified variants can include polymorphic variants, interspecies homologs (orthologs), intraspecies homologs (paralogs), and allelic variants.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or proteins, refer to two or more sequences or subsequences that are the same or have a specified percentage of nucleotides or amino acids that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST/. Such sequences are then said to be "substantially identical." This definition also refers to, or may be applied to, the compliment of a test sequence. The definition also includes sequences that have deletions and/or additions, as well as those that have substitutions. Preferred algorithms can account for gaps and the like. Identity is typically calculated over a region that is at least about 25 amino acids or nucleotides in length, or more preferably over a region that is 50-100 amino acids or nucleotides in length, or over the entire length of a given sequence.

A "control" sample or value refers to a sample that serves as a reference, usually a known reference, for comparison to a test sample. For example, a test sample can include a solution comprising glycoprotein exposed to a polypeptide with an endoglycosidase domain (e.g., SEQ ID NO:1 or SEQ ID NO:2), while the control sample does not include the polypeptide, or includes a different, known glycan-cleaving domain. In another example, a test sample can be taken from a patient sensitive to a particular glycoprotein, and compared to samples from a known normal (non-sensitive) individual. A control can also represent an average value gathered from a population of similar individuals, e.g., patients or healthy individuals with a similar medical background, same age, weight, etc. A control value can also be obtained from the same individual, e.g., from an earlier-obtained sample, prior to onset of the targeted condition or symptom, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "pharmaceutical" composition is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose will generally refer to the amount of antibiotic or anti-inflammatory agent, though dosage can also be expressed in terms of bacterial concentration. The dose will vary depending on a number of factors, including frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat," "therapeutic," "prevent," and "prophylactic" are not intended to be absolute terms. The terms can refer to any delay in onset, reduction in the frequency or severity of adverse symptoms, improvement in patient comfort, etc. The effect of treatment can be compared to an individual or pool of individuals not receiving a given treatment, or to the same patient prior to, or after cessation of, treatment.

The term "therapeutically effective amount," as used herein, refers to that amount of the therapeutic agent sufficient to ameliorate the targeted condition or symptoms. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

III. Deglycosylating Enzymes

The presently disclosed deglycosylating enzymes belong to the GH18 and GH85 families of endoglycosidases. These enzymes are capable of cleaving a much broader range of N-glycans from N-glycosylated proteins than previously characterized deglycosylating enzymes.

N-glycosylation of proteins is common in eukaryotes, but also observed in bacteria. N-glycosylation is involved in protein folding, targeting of the glycoprotein to the membrane or for secretion, resistance to proteolysis, cell adhesion, intracellular signaling, and antigen presentation. N-glycoproteins include milk proteins (e.g., lactoferrin, IgA, and whey), immunoglobulins, and plant proteins (e.g., soy protein).

N-glycans are divided into three classes: high (or oligo) mannose, complex, and hybrid. All three share a core molecule of two N-acetylglucosamines and three mannose residues ($Man_3GlcNAc_2$), which form two branches. High mannose N-glycans comprise mannose saccharides in both branches. Complex N-glycans include additional types of saccharides, e.g., D-glucose (Glc), D-galactose (Gal), Mannose, L-fucose (Fuc), sialic acid (e.g., N-acetylneuraminic acid (NeuAc)), N-acetylgalactosamine, and additional N-acetylglucosamines (GlcNAC), in both branches. Additional saccharides are in less complex organisms. Hybrid N-glycans have a mannose branch and a complex branch.

The presently disclosed deglycosylating enzymes are unique in that they remove all three types of N-glycans. In some embodiments, the present deglycosylating enzymes cleave N-glycans with terminal fucosylation and/or sialylation, and/or core fucosylation.

Accordingly, provided herein are deglycosylating enzymes with a broad N-glycan substrate range, i.e., capable of cleaving high mannose, complex, and hybrid N-glycans from a protein. In some embodiments, the deglycosylating enzyme is a GH18 endoglycosidase polypeptide comprising a sequence of GLDIDME (SEQ ID NO:1). In some embodiments, the polypeptide lacks a transmembrane domain that spans a cell membrane (i.e., the polypeptide is not present in its natural form spanning a membrane of a cell). In some embodiments, the polypeptide comprises a sequence having greater than 85% identity, e.g., 90, 91, 92, 93, 94, 95, 96, 97, 98, 99, or 100%, to a sequence selected from the group consisting of SEQ ID NO:7-20. In some embodiments, the polypeptide comprises a sequence having greater than 85% identity to SEQ ID NO:7 or SEQ ID NO:15. In some embodiments the polypeptide comprises SEQ ID NO:7. In some embodiments, the polypeptide comprises SEQ ID NO:15. In some embodiments, the polypeptide comprises a sequence having greater than 85% identity, e.g., 90, 91, 92, 93, 94, 95, 96, 97, 98, 99, or 100%, to SEQ ID NO:4 or SEQ ID NO:5. In some embodiments, the polypeptide comprises SEQ ID NO:4. In some embodiments, the polypeptide comprises SEQ ID NO:5.

In some embodiments, the deglycosylating enzyme with a broad N-glycan substrate range is a GH85 endoglycosidase polypeptide comprising a sequence of FINQET (SEQ ID NO:2). In some embodiments, the polypeptide lacks a transmembrane domain that spans a cell membrane (i.e., the polypeptide is not present in its natural form spanning a membrane of a cell). In some embodiments, the polypeptide comprises a sequence having greater than 85% identity, e.g., 90, 91, 92, 93, 94, 95, 96, 97, 98, 99, or 100%, to a sequence selected from the group consisting of SEQ ID NO:21-31. In some embodiments, the polypeptide comprises a sequence having greater than 85% identity to SEQ ID NO:29. In some embodiments the polypeptide comprises SEQ ID NO:29. In some embodiments, the polypeptide comprises a sequence having greater than 85% identity, e.g., 90, 91, 92, 93, 94, 95, 96, 97, 98, 99, or 100%, to SEQ ID NO:6. In some embodiments, the polypeptide comprises SEQ ID NO:6.

In some embodiments, the polypeptide is in an in vitro solution with an N-glycoprotein, wherein the N-glycoprotein comprises a high mannose, complex, and/or hybrid N-glycan. For example, a GH18 or GH85 endoglycosidase as described herein can be used in a laboratory or industrial setting to cleave N-glycans from N-glycoproteins, creating over time a solution of endoglycosidase, a decreasing amount of N-glycoproteins, and increasing amounts of free glycans and deglycosylated proteins. In some embodiments, the N-glycan comprises core fucosylation, terminal fucosylation, or terminal sialylation. The polypeptide, while not spanning a cell membrane in its natural form, can include a transmembrane domain. In some embodiments, the polypeptide can be linked to a substrate, e.g. a bead or plate surface.

In some embodiments, the deglycosylating enzyme with a broad N-glycan substrate range is a GH18 endoglycosidase polypeptide comprising a sequence of GLDIDME (SEQ ID NO:1) and is recombinantly expressed in a cell. In some embodiments, the polypeptide spans the membrane of the cell. In some embodiments, the polypeptide comprises a sequence having substantial identity (e.g., greater than 85% identity, e.g., 90, 91, 92, 93, 94, 95, 96, 97, 98, 99, or 100%) to a sequence selected from the group consisting of SEQ ID NO:7-20. In some embodiments, the polypeptide comprises a sequence having greater than 85% identity to SEQ ID NO:7 or SEQ ID NO:15. In some embodiments the polypeptide comprises SEQ ID NO:7. In some embodiments, the polypeptide comprises SEQ ID NO:15. In some embodiments, the polypeptide comprises a sequence having greater than substantial identity (e.g., greater than 85% identity, e.g., 90, 91, 92, 93, 94, 95, 96, 97, 98, 99, or 100%) to SEQ ID NO:4 or SEQ ID NO:5. In some embodiments, the polypeptide comprises SEQ ID NO:4. In some embodiments, the polypeptide comprises SEQ ID NO:5. In some embodiments, the polypeptide comprises a sequence having substantial identity (e.g., greater than 85% identity, e.g., 90, 91, 92, 93, 94, 95, 96, 97, 98, 99, or 100%) to the full length mature polypeptide sequence of EndoBI-1 or EndoBI-2.

In some embodiments, the deglycosylating enzyme with a broad N-glycan substrate range is a GH85 endoglycosidase polypeptide comprising a sequence of FINQET (SEQ ID NO:2) and is recombinantly expressed in a cell. In some embodiments, the polypeptide spans the membrane of the cell. In some embodiments, the polypeptide comprises a sequence having substantial identity (e.g., greater than 85% identity, e.g., 90, 91, 92, 93, 94, 95, 96, 97, 98, 99, or 100%) to a sequence selected from the group consisting of SEQ ID NO:21-31. In some embodiments, the polypeptide comprises a sequence having greater than 85% identity to SEQ ID NO:29. In some embodiments the polypeptide comprises SEQ ID NO:29. In some embodiments, the polypeptide comprises a sequence having substantial identity (e.g., greater than 85% identity, e.g., 90, 91, 92, 93, 94, 95, 96, 97, 98, 99, or 100%) to SEQ ID NO:6. In some embodiments, the polypeptide comprises SEQ ID NO:6.

In some embodiments, the polypeptide recombinantly expressed in a cell is in an in vitro solution with an N-glycoprotein, wherein the N-glycoprotein comprises a high mannose, complex, and/or hybrid N-glycan. For example, recombinant cells expressing a GH18 or GH85 endoglycosidase as described herein can be used in a laboratory or industrial setting to cleave N-glycans from N-glycoproteins, creating over time a solution of cells, a decreasing amount of N-glycoproteins, and increasing amounts of free glycans and deglycosylated proteins. In some embodiments, the N-glycan comprises core fucosylation, terminal fucosylation, or terminal sialylation.

The deglycosylating enzymes described herein can be used for generating free glycans, generating deglycosylated polypeptides for use in nutritional, prophylactic, or therapeutic applications. The deglycosylating enzymes can also be used for proteomic or glycoproteomic studies, providing a one-step deglycosylation that facilitates characterization of proteins or glycans that are normally inaccessible or that normally require multiple enzymatic or chemical treatments before study.

IV. Methods of Making Recombinant Enzymes

The deglycosylating enzymes described herein can be recombinantly expressed and produced using methods well known in the art. Routine techniques in the field of recombinant protein expression and production can be found, e.g., in Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999).

Bifidobacteria are designated GRAS, and thus can be used for recombinant expression of the presently described deglycosylating enzymes. Exemplary *Bifidobacteria* (e.g., *Bifidobacteria* recombinantly expressing a deglycosylating enzyme) can include, but are not limited to, *B. longum* bv *infantis*, *B. longum* bv *longum*, *B. breve*, and *B. adolescentis*.

One of skill will recognize, however, that many eukaryotic and prokaryotic cells can be used for routine cloning, expression, and production of the deglycosylating enzymes disclosed herein. These include animal cells, insect cells, bacteria, fungi, and yeasts, many of which are commercially available. For example, common laboratory strains of E. coli, yeast, or mammalian cells can be used to produce the recombinant deglycosylating enzymes. Methods for introduction and expression of isolated or heterologous nucleic acids in a cell are well-known, and can be found, for example, in the general reference, supra. Accordingly, this invention also provides for host cells and expression vectors comprising the nucleic acid sequences described herein.

Nucleic acids encoding the presently described deglycosylating enzymes can be made using standard recombinant or synthetic techniques. Nucleic acids may be RNA, DNA, or hybrids thereof. One of skill can construct a variety of clones containing functionally equivalent nucleic acids, such as nucleic acids that encode the same polypeptide. Cloning methodologies to accomplish these ends, and sequencing methods to verify the sequence of nucleic acids are well known in the art.

In some embodiments, the nucleic acids are synthesized in vitro. Deoxynucleotides may be synthesized chemically according to the solid phase phosphoramidite triester method described by Beaucage & Caruthers, *Tetrahedron Letts.* 22(20):1859-1862 (1981), using an automated synthesizer, e.g., as described in Needham-VanDevanter, et al., *Nucleic Acids Res.* 12:6159-6168 (1984). In other embodiments, the desired nucleic acid sequence may be obtained by an amplification reaction, e.g., PCR.

One of skill will be familiar with methods for generating alterations or variants of a given polynucleotide or polypeptide sequence, e.g., for optimal expression in a given cell.

To obtain high level expression of a desired sequence (e.g., a sequence that results in ablation of PGCs), an expression vector is constructed that includes such elements as a promoter to direct transcription, a transcription/translation terminator, a ribosome binding site for translational initiation, and the like. Suitable bacterial promoters are well known in the art and described, e.g., in the references providing expression cloning methods and protocols cited hereinabove. Kits for such expression systems are commercially available. Eukaryotic expression systems for mammalian cells, yeast, and insect cells are well known in the art and are also commercially available.

In addition to the promoter, the expression vector typically contains a transcription unit or expression cassette that contains all the additional elements required for expression of the nucleic acid in host cells. A typical expression cassette thus contains a promoter operably linked to the nucleic acid sequence encoding the protein or inhibitory polynucleotide, and signals required for efficient polyadenylation of the transcript, ribosome binding sites, and translation termination.

The expression cassette can contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET15b, pET23D, pET-22b(+), and fusion expression systems such as GST and LacZ. Epitope tags can also be added to recombinant proteins to provide convenient methods of isolation, e.g., 6-his. These vectors comprise, in addition to the expression cassette containing the coding sequence, the T7 promoter, transcription initiator and terminator, the pBR322 ori site, a bla coding sequence and a lacI operator.

The expression vectors or plasmids of the invention can be transferred into the chosen host cell by well-known methods such as calcium chloride transformation for *E. coli* and calcium phosphate treatment, liposomal fusion or electroporation for mammalian cells. Cells transformed by the plasmids can be selected by resistance to antibiotics conferred by genes contained on the plasmids, such as the amp, gpt, neo and hyg genes.

The expression level of a gene can be determined by detecting mRNA, protein, or activity according to techniques known in the art. For example, mRNA levels can be detected using Northern blots, reverse transcription PCR (RTPCR), or quantitative RTPCR (sometimes called real time PCR). Such techniques are reviewed, e.g., in VanGuilder et al. (2008) *Biotechniques* 44:619 and *Real-Time PCR: Current Technology and Applications*, Caister Academic Press (2009). Protein levels can be detected using antibody-based assays, e.g., Western blots or ELISAs. In some embodiments, protein expression can be detected by detecting an operably-linked protein label, e.g., GFP, 6-histine, or biotin.

In some embodiments, the recombinantly produced deglycosylating enzyme can be purified from the cell, e.g., separated from other cellular components, using known techniques. For example, where the deglycosylating enzyme lacks a transmembrane domain, the enzyme is typically isolated and used separately from the recombinant cell. In some embodiments, the recombinantly produced deglycosylating enzyme includes a transmembrane domain, and the deglycosylating enzyme-expressing cell is used.

V. Prebiotic and Probiotic Compositions and Applications

As indicated above, the presently described deglycosylating enzymes, as well as the free glycans and/or deglycosylated proteins released by the enzymes, can be used for nutritional, prophylactic and therapeutic purposes.

The deglycosylating enzymes described herein can be involved in modulating protein stability and immune recognition of N-glycosylated proteins, e.g., in a host organism. For example, recognition of Gram-positive bacteria by IgA is dependent on its glycosylation (Mathias & Corthesy, *J Biol Chem* 286:17239-17247 (2011)). Intracellular signaling and NF-kB activation of the toll-like receptor 3 (Sun et al., *J Biol Chem* 281:11144-11151 (2006)) is modulated by N-glycans. C-type lectins, galectins and sialic-acid-binding Ig-like lectins are immune and cell response mediators that specifically recognize different epitopes in N-glycans (Varki, *Essentials of glycobiology* (Cold Spring Harbor Laboratory Press, Cold Spring Harbor, N.Y.) 2nd Ed pp xxix, 784 p. (2009)). Accordingly, the presently described deglycosylating enzymes can be administered to an individual, either in isolated form, or recombinantly expressed in a cell to modulate immune recognition and/or signaling and/or processing of glycosylated proteins.

In some embodiments, the compositions of the invention are administered to those in need stimulation of the immune system and/or for promotion of resistance to bacterial or yeast infections, e.g., Candidiasis or diseases induced by sulfate reducing bacteria.

Glycans produced by the presently described deglycosylating enzymes can be administered as a prebiotic formulation (i.e., without bacteria) or as a probiotic formulation (i.e., with desirable bacteria such as *Bifidobacteria* or other food grade bacteria). In addition, a probiotic formulation can include recombinant cells (e.g., *Bifidobacteria* or other food grade bacteria) expressing a deglycosylating enzyme as described herein.

Glycans (or oligosaccharides) produced by the presently described deglycosylating enzymes can be isolated and used separately or individually. N-glycans come in a wide variety of structures and sizes, and can include complex oligosaccharide structures. Deglycosylating enzymes isolated from beneficial gut bacteria, such as *Bifidobacteria*, typically produce N-glycans that stimulate growth of the beneficial bacteria, as well as deglycosylated proteins that can be more readily digested by the host.

Examples of free N-glycans that can be used individually or in any combination are those listed in the Tables in Example 8, which describes the composition of N-glycans freed from bovine milk glycoproteins by the EndoBI-1 enzyme. Additional examples of free N-glycans that can be used individually or in any combination are those shown in FIGS. 4 and 5. The milk oligosaccharides described in U.S. Pat. No. 8,197,872 and WO2012/009315 provide additional examples.

In some embodiments, provided herein are prebiotic or probiotic compositions comprising at least one of the free N-glycans generated by the presently described deglycosylating enzymes, e.g., an oligosaccharide consisting of 3 Hex (glucose, galactose, or mannose) moieties and 5 HexNAc (GlcNac or GalNAc) moieties;

an oligosaccharide consisting of 4 Hex moieties, 4 HexNAc moieties;

an oligosaccharide consisting of 4 Hex moieties, 4 HexNAc moieties, and 1 NeuAc (N-acetylneuraminic acid) moiety;

an oligosaccharide consisting of 5 Hex moieties, 3 HexNAc moieties, and 1 NeuAc moiety;

an oligosaccharide consisting of 4 Hex moieties, 3 HexNAc moieties, and 1 NeuAc moiety;

an oligosaccharide consisting of 3 Hex moieties, 5 HexNAc moieties, and 1 NeuAc moiety;

an oligosaccharide consisting of 5 Hex moieties, 1 Fuc (fucose) moiety, 3 HexNAc moieties, and 1 NeuGc (N-glycolylneuraminic acid) moiety; and an oligosaccharide consisting of 5 Hex moieties, 3 HexNAc moieties, and 2 NeuAc moieties.

In some embodiments the prebiotic or probiotic composition comprises at least 2, 3, 4, 5, 6, 7, 8, 9, or 10 of the free N-glycans generated by the presently described deglycosylating enzymes. In some embodiments, provided herein is a composition comprising free N-glycans, wherein said free N-glycans are produced by contacting a deglycosylating enzyme (e.g., a GH18a, GH18b, or GH85 enzyme) with milk. In some embodiments, the composition comprises the free N-glycans separated from the remaining milk components. In some embodiments, the composition comprises free N-glycans and deglycosylated milk proteins.

In general, any food or beverage that can be consumed by human infants or adults or animals can be used to make formulations containing such prebiotic and probiotic compositions. Exemplary foods include those with a semi-liquid consistency to allow easy and uniform dispersal of the prebiotic and probiotic compositions of the invention. However, other consistencies (e.g., powders, liquids, etc.) can also be used without limitation. Accordingly, such food items include, without limitation, dairy-based products such as cheese, cottage cheese, yogurt, and ice cream, nut-containing formulations such as peanut butter, plant-based products such as tofu or other soy products, and egg-containing formulations, e.g., custards and processed egg products. Processed fruits and vegetables, including those targeted for infants/toddlers, such as apple sauce or strained peas and carrots, are also suitable for use in combination with the prebiotic and probiotic formulations. In addition to foods targeted for human consumption, animal feeds may also be supplemented with the prebiotic and probiotic compositions of the invention.

The prebiotic and probiotic compositions can also be used to supplement a beverage. Examples of such beverages include, without limitation, infant formula, follow-on formula, toddler's beverage, milk, soy milk, fermented milk, fruit juice, fruit-based drinks, and sports drinks. Many infant and toddler formulas are known in the art and are commercially available, including, for example, Carnation Good Start (Nestle Nutrition Division; Glendale, Calif.) and Nutrish A/B produced by Mayfield Dairy Farms (Athens, Tenn.). Other examples of infant or baby formula include those disclosed in U.S. Pat. No. 5,902,617. Other beneficial formulations of the compositions of the present invention include the supplementation of animal milks, such as cow's milk.

The prebiotic and probiotic compositions can be formulated into pills or tablets or encapsulated in capsules, such as gelatin capsules. Tablet forms can optionally include, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The inventive prebiotic or probiotic formulations can also contain conventional food supplement fillers and extenders such as, for example, rice flour. Suitable formulations can be found, e.g., in Remington's Pharmaceutical Sciences, Mack Publishing Company, Philadelphia, Pa., $17^{th}$ Ed. (1985).

The dosages of the prebiotic and probiotic compositions of the present invention will be varied depending upon the requirements of the individual and will take into account factors such as age (infant versus adult), weight, and reasons for loss of beneficial gut bacteria (e.g., antibiotic therapy, chemotherapy, disease, or age). In some embodiments, the amount administered to an individual should be sufficient to establish colonization of the gut with beneficial bacteria over time. The size of the dose also will be determined by the existence, nature, and extent of any adverse side-effects that may accompany the administration of a prebiotic or probiotic composition described herein. In some embodiments, the dosage range will be effective as a food supplement and for reestablishing beneficial bacteria in the intestinal tract.

In some embodiments, the dose of free N-glycans can range from about 1 micrograms/L to about 25 grams/L of galacto-oligosaccharides. In some embodiments, the dose of free N-glycans is about 100 micrograms/L to about 15 grams/L. In some embodiments, the dose of free N-glycans is 1 gram/L to 10 grams/L. Exemplary dosages of recombinant cells (e.g., *Bifidobacteria*) expressing the deglycosylating enzymes described herein include, but are not limited to, $10^4$ to $10^{12}$ colony forming units (CFU) per dose, e.g., $10^6$ to $10^{10}$ CFU per dose. Examples of N-glycans are milk oligosaccharides, e.g., from a human (HMO), bovine, or ovine.

The prebiotic or probiotic formulations of the invention can be administered to any individual in need thereof. In some embodiments, the individual is an infant or toddler. For example, in some embodiments, the individual is less than, e.g., 3 months, 6 months, 9 months, one year, two years or three years old. In some embodiments, the individual is an adult. For example, in some embodiments, the individual is over 50, 55, 60, 65, 70, or 75 years old. In some embodiments, the individual is immuno-deficient (e.g., the individual has AIDS or is taking chemotherapy).

Exemplary *Bifidobacteria* (e.g., *Bifidobacteria* recombinantly expressing a deglycosylating enzyme) that can be included in the probiotic compositions of the invention include, but are not limited to, *B. longum* by *infantis*, *B. longum* by *longum*, *B. breve*, and *B. adolescentis*. The *Bifidobacterium* used can depend in part on the target consumer. For example, a *B. longum* by *infantis* probiotic is typically administered to an infant or young child (e.g., under 5 years old). In some embodiments, *B. longum* by *infantis* is included in, or in conjunction with, an infant formula or follow-on formula. In some embodiments, the probiotic composition administered to an adult or an elderly person. In some embodiments, the person is at least 50, 60, 70, or 80 years old. One of skill will recognize that the bacterial strain is not crucial as long as it expresses a deglycosylating enzyme as described herein.

It will be appreciated that it may be advantageous for some applications to include other Bifidogenic factors in the formulations of the present invention. Such additional components may include, but are not limited to, fructoligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as lactose, xylooligosaccharides, soyoligosaccharides, lactulose/lactitol, among others.

In some embodiments, the compositions of the invention are administered to a human or animal in need thereof. For example, in some embodiments, the compositions of the invention are administered to a person or animal having at least one condition selected from the group consisting of inflammatory bowel syndrome, constipation, diarrhea, colitis, Crohn's disease, colon cancer, functional bowel disorder (FBD), irritable bowel syndrome (IBS), excess sulfate reducing bacteria, inflammatory bowel disease (IBD), and ulcerative colitis. Irritable bowel syndrome (IBS) is characterized by abdominal pain and discomfort, bloating, and altered bowel function, constipation and/or diarrhea. There are three groups of IBS: Constipation predominant IBS (C-IBS), Alternating IBS (A-IBS) and Diarrhea predominant IBS (D-IBS).

VI. Kits

The deglycosylating enzymes described herein can be included as part of a kit, e.g., for generating free glycans and/or deglycosylated polypeptides. In some embodiments, the kit includes an expression vector comprising a coding sequence for a deglycosylating enzyme described herein (e.g., an endoglycosidase comprising an amino acid sequence of SEQ ID NO:1 or 2 with broad substrate specificity). In some embodiments, the kit includes a recombinant cell comprising such an expression vector. In some embodiments, the kit includes the deglycosylating enzyme, e.g., in a buffer or lyophilized form.

In some embodiments, the kit includes a control, e.g., a set of standard free glycans, standard glycoproteins, standard deglycosylated proteins, or another deglycosylating enzyme (e.g., one with a limited substrate specificity).

In some embodiments, the kit can include components for separating free glycans and deglycosylated proteins, e.g., affinity based or size based separation components such as spin columns or chromatography reagents. Where the presently disclosed enzymes are to be used to generate free glycans and/or deglycosylated proteins for further characterization, the kit can further include buffers for the free glycans and/or deglycosylated proteins. In some embodiments, the kit can include reagents for further characterization, e.g., gel or reagents for size determination, reagents for preparation of a sample for MALDI analysis, etc.

In some embodiments, the kit can be used for generating free glycans and/or deglycosylated proteins for administration (e.g., as a food product, prophylactic or therapeutic agent). In such cases, the kit can include pharmaceutically acceptable excipients and/or buffers.

Such kits can also include standard reagents for recombinant techniques, e.g., expression vector, media, buffers, etc. Kits often also include instructions for using components of the kits, e.g., for optimal application-dependent deglycosylating conditions. The kit can also include consumables, such as tubes, pipettes, and/or glassware for carrying out the methods of the invention.

It is understood that the examples and embodiments described herein are for illustrative purposes only and that various modifications or changes in light thereof will be suggested to persons skilled in the art and are to be included within the spirit and purview of this application and scope of the appended claims. All publications, sequence database entries, internet sites, patents, and patent applications cited herein are incorporated by reference in their entireties for all purposes.

VII. EXAMPLES

A. Example 1. Infant Isolates of *Bifidobacteria* Display endo-N-acetylglucosaminidase Activity Bovine ribonuclease B (RNAseB) is a 17 kDa glycoprotein that contains one glycosylation site, composed of high mannose N-linked glycans. Cleavage by endoglycosidases results in a molecule of 14 kDa. Overnight incubations of bifidobacterial isolates with RNAseB suggested that endoglycosidase activity is present in only some isolates. None of the *B. bifidum* strains examined displayed this phenotype, and *B. infantis* strains degraded RNAseB weakly. Incubation of *B. infantis* ATCC 15697 with 5 mg/ml of RNAseB led to a gradual deglycosylation of this glycoprotein over time (FIG. 1A). Certain isolates of *B. breve* such as KA179 and JCM7019, completely deglycosylated RNAseB (FIG. 1B-D).

Distribution of endo-N-acetylglucosaminidase gene sequences in *bifidobacteria*. Protein sequences of endo-N-acetylglucosaminidases found in the sequenced genomes of *Bifidobacterium* were aligned and degenerated primers designed to amplify conserved regions (see Tables 1-3). PCR products from 77 isolates of *Bifidobacteria* (Table 4) were sequenced, and full gene sequences were determined using a DNA-walking approach. Several isolates encoded proteins belonging to glycohydroase family 18 (GH18) or 85

(GH85). All strains containing one of these sequences also cleaved RNAseB in vitro, and strains lacking such genes did not show endoglycosidase activity, indicating that the GH18 or GH85 type enzymes were responsible for the observed RNaseB cleavage.

A phylogenetic tree (FIG. 1D) classified these protein sequences in three types. One group was exclusively found in B. infantis strains including the sequence found in strain ATCC 15697 (termed GH18a), which are related to EndoE. Another group of sequences contained in strains of B. infantis, B. breve and B. longum also belong to family GH18, but with only 60% similarity to GH18a, was termed GH18b. Sequences belonging to GH85 were almost exclusively found in B. breve isolates. Multiple alignments revealed a high degree of conservation of the proposed active site for each glycosidase family (Table 1). The genomic landscape for these genes also supports their linkage to glycan consumption. The gene from B. infantis ATCC 15697, Blon_2468, is in a gene cluster that also contains a phosphotransferase (PTS) system specific for N-acetylglucosamine (FIG. 2). BLIF_1310 in B. infantis 157F (GH18b), and BLD_0197 in B. longum DJO10A (GH85) are located near ABC transporters predicted to import oligosaccharides and two or three α-mannosidases (FIG. 2).

Figure 3B:
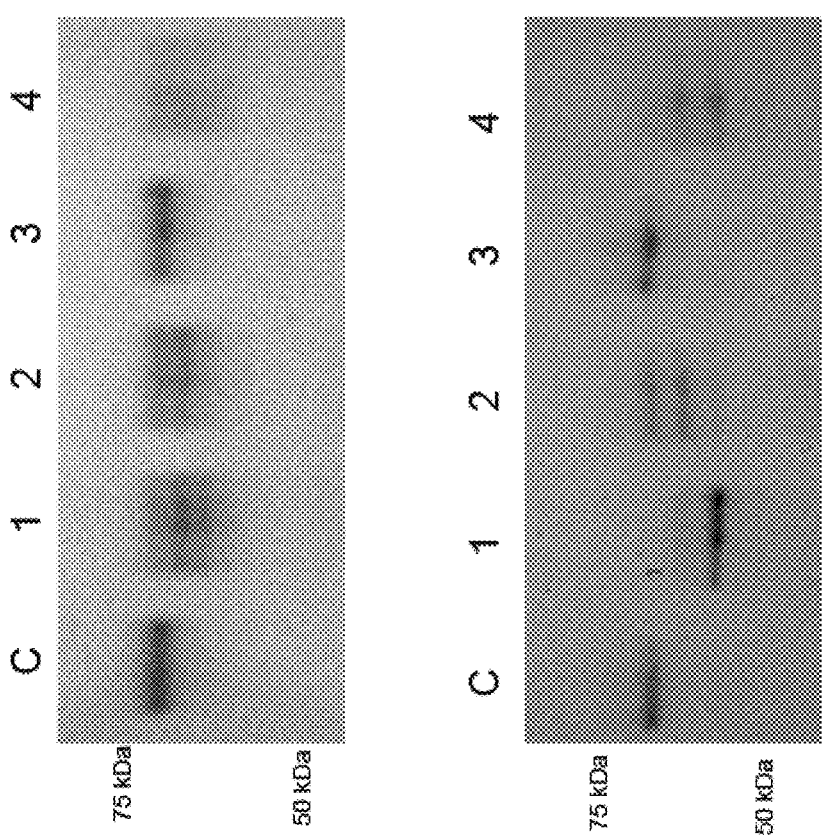
FIG. 3A-3B: Characterization of recombinant endoglycosidases in *bifidobacteria*. A: Heat tolerance of EndoBI-1, EndoBI-2 or EndoBB evaluated in SDS-PAGE gels. B: Coincubations of bLF and hLF with EndoBI-1 (1), EndoBI-2 (2), EndoBB (3) or PNGaseF (4). Control (C) non digested reactions were included in parallel.
Figure 3A:
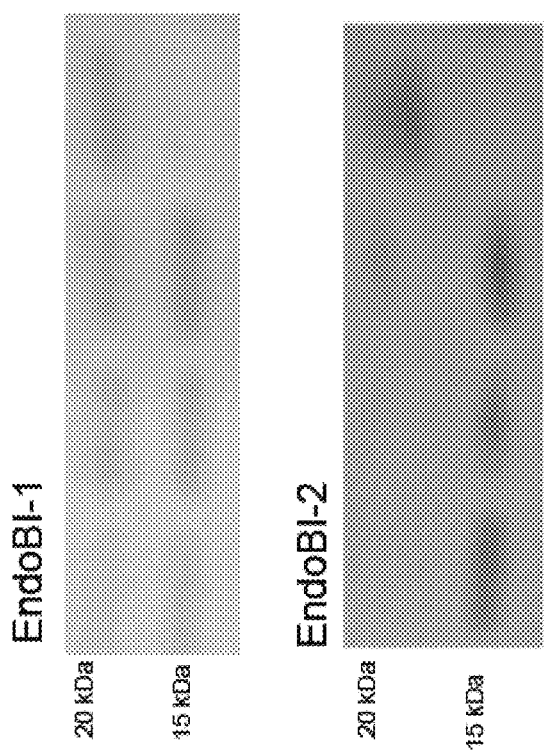

B. Example 2: Enzymatic Properties of Bifidobacterial endo-N-acetylglucosaminidases Based on the sequence alignments (FIG. 1D), a representative gene of each group was cloned, expressed and purified in E. coli. The endo-β-N-acetylglucosaminidases from B. infantis ATCC 15697 (EndoBI-1), B. infantis SC142 (EndoBI-2), and B. breve (EndoBB) all exhibited a maximum glycolytic activity at pH 5.0 and optimal temperatures ranging from 37 to 45° C. An interesting property of EndoBI-1 and EndoBI-2 was that their activity was not significantly impaired by incubation at 95° C. for 5 minutes, suggesting that they are heat resistant enzymes (FIG. 3A). Properties of EndoBI-1, EndoBI-2 and EndoBB

|  | EndoBI-1 | EndoBI-2 | EndoBB |
|---|---|---|---|
| Family | GH18 | GH18 | GH85 |
| Calculated MW (recombinant protein) | 47 kDa | 47 kDa | 98 kDa |
| Transmembrane domains | 2 | 2 | 1 |
| Optimum pH | 5.0 | 5.0 | 5.0 |
| Optimum temperature | 37-45° C. | 37-45° C. | 30-45° C. |
| Heat resistance | Yes | Yes | No |

Human lactoferrin (hLF) contains core fucosylated complex N-glycans, predominantly in two glycosites (Yu et al., Glycobiology 21:206-224 (2011)). Bovine lactoferrin (bLF) represents a minor fraction of bovine milk, and it contains high mannose and hybrid N-linked glycans at five glycosites (Nwosu et al., J Proteome Res 10:2612-2624 (2011)). Overnight incubations of bLF and hLF with the three Bifidobacterium endoglycosidases indicated that all of them were able to cleave bLF, as observed by discrete changes in MW on SDS-PAGE gels (FIG. 3B). EndoBI-1 and EndoBI-2 cleaved hLF (FIG. 3C).

Figure 4B:
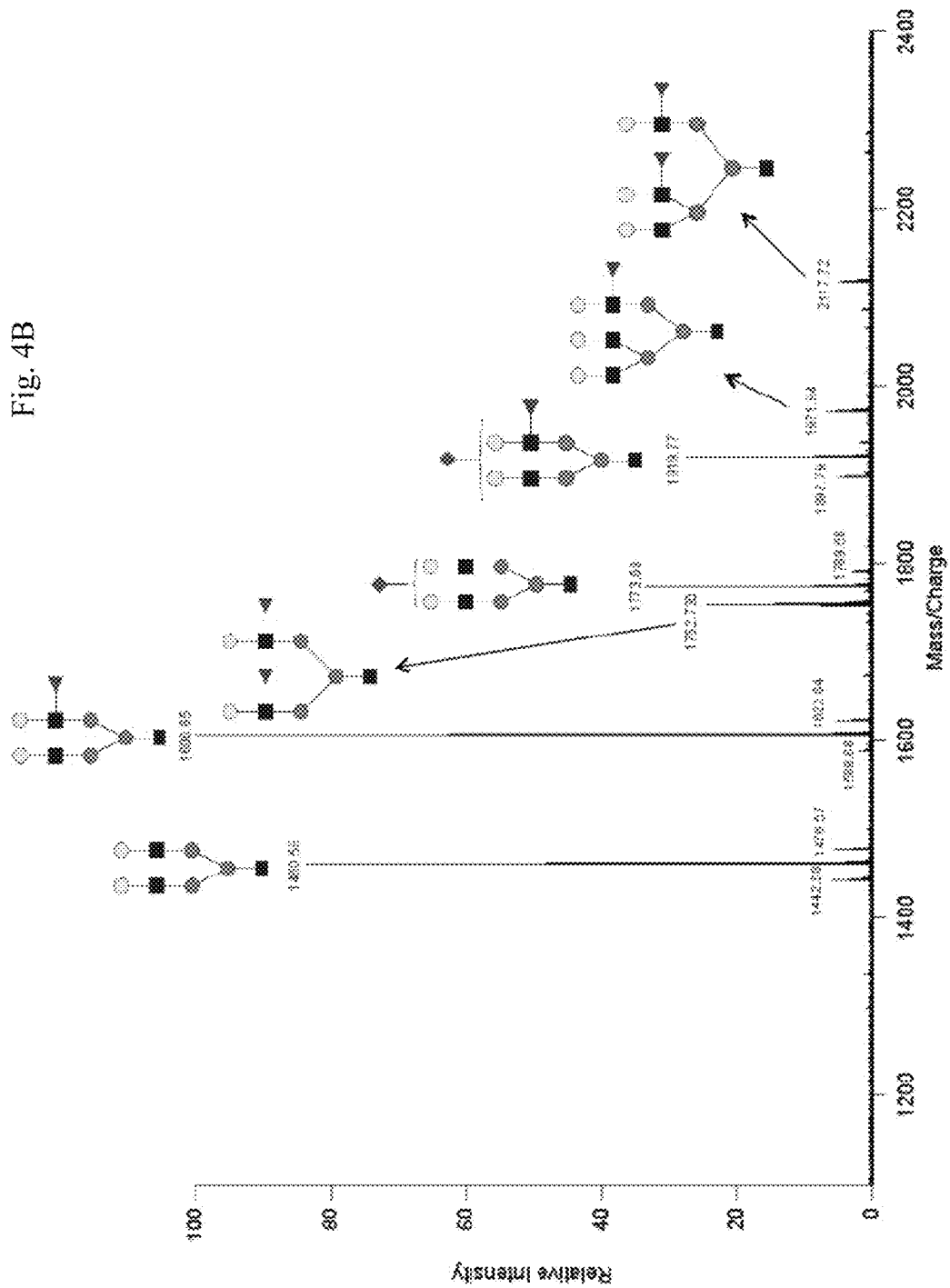
Figure 5B:
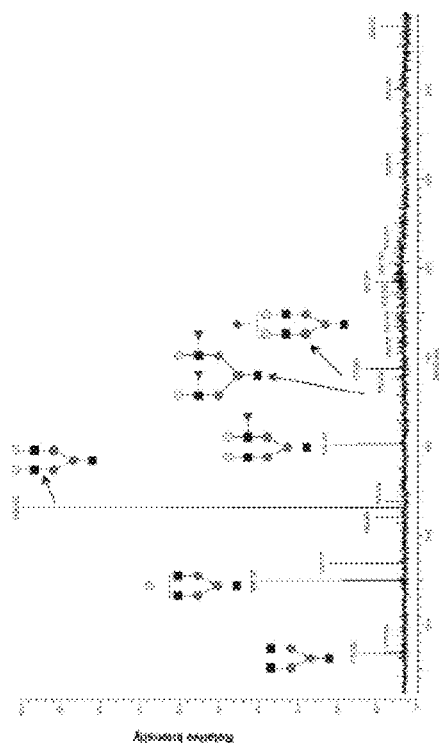
FIG. 5A-5D: MALDI of free glycans released from (A) RNAseB, (B) IgG, (C) hLF in negative mode, and (D) IgA in negative mode upon exposure to EndoBI-1.
Figure 5D:
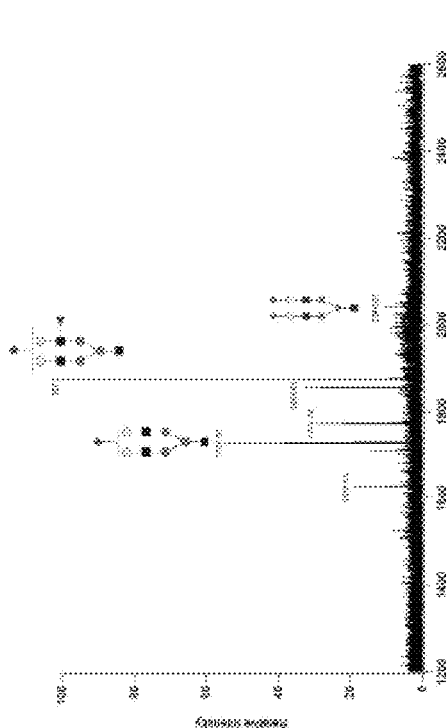
Figure 5A:
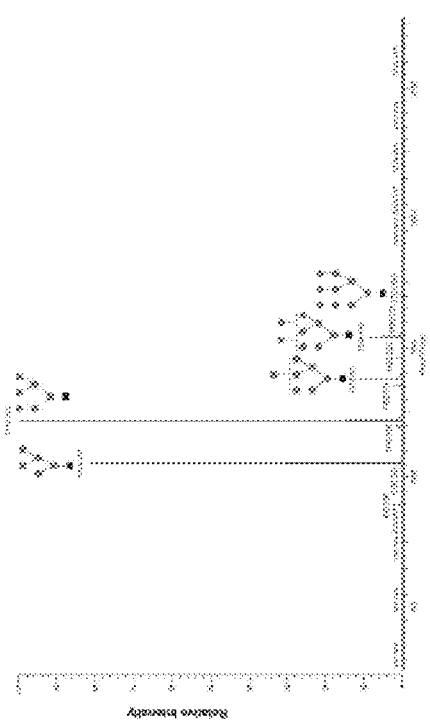
Figure 5C:
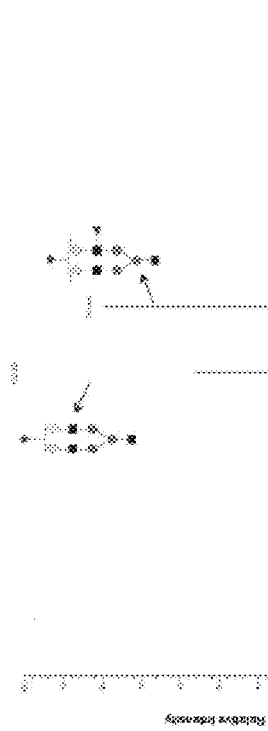

C. Example 3: EndoBI-1 Cleaves the Chitobase Core in High Mannose and Complex N-glycans FIGS. 4 and 5 show mass spectrometry (MALDI) data of N-glycans released from various N-glycoproteins by EndoBI-1. FIG. 4 shows results from (A) bLF, (B) hLF, and (C) IgA, while FIG. 5 shows results from (A) RNAseB, (B) IgG, (C) hLF in negative mode, and (D) IgA in negative mode.

D. Example 4: EndoBI-1 Binds Specifically the Core of N-Linked Glycans

Figure 6A:
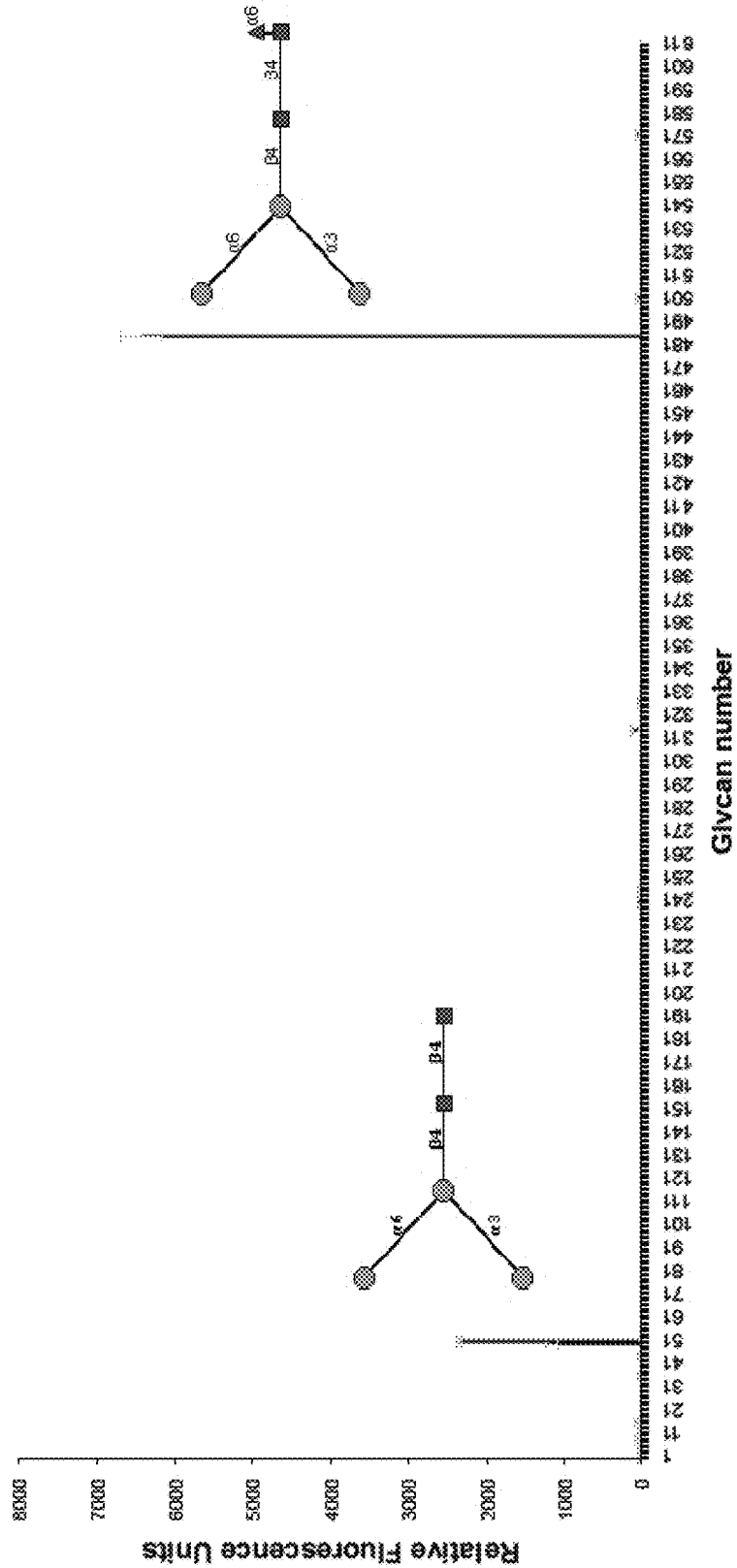
FIG. 6A-6B: Properties of D184N mutant EndoBI-1. (A) Glycan array analysis of EndoBI-1 D184N binding to mammalian glycans (x-axis). Bars represent SD of sextuplicates. (B) Binding of EndoBI-1 or EndoBI D184N to coated glycoproteins, as detected by a FITC-AntiHis antibody. Error bars represent SD from triplicate experiments. Astrices represent samples with $p<0.05$ compared to BSA.
Figure 6B:
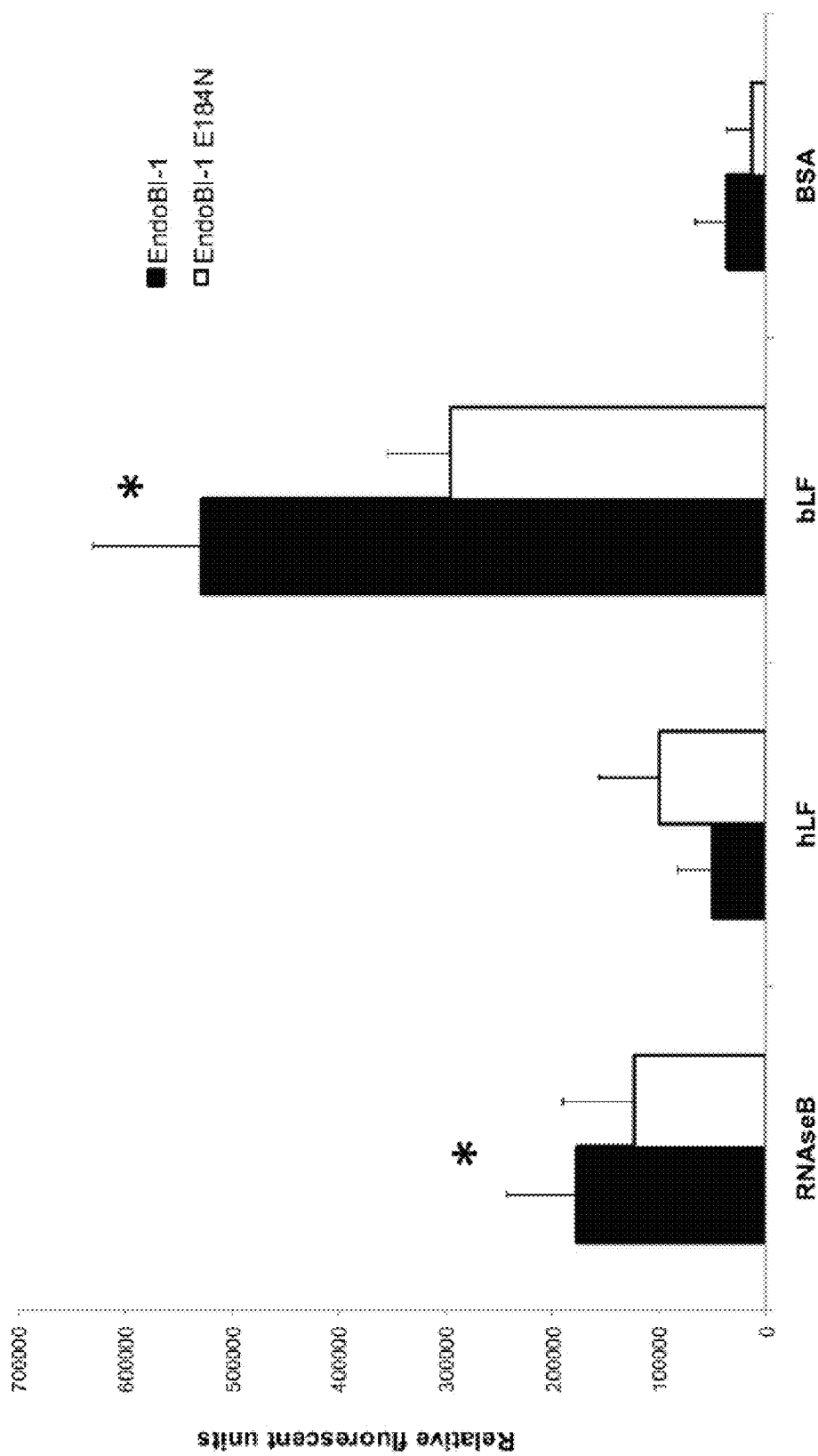

The conserved active site in GH18 enzymes includes a D-X-E motif, where D and E have been reported to be necessary for activity. Asp184 in EndoBI-1 was mutated by site-directed mutagenesis to Asn184 (EndoBI-1 mut or EndoBI-1 D184N). The mutant enzyme specifically bound to the core of N-glycans, Man$_3$GlcNAc$_2$ on a mammalian glycan array (FIG. 6A). EndoBI-1 D184N also showed significant binding to the α1-6 fucosylated pentasaccharide, characteristic of human N-linked glycoproteins. When equimolar amounts of RNAseB, bLF and hLF were coated to microwell plates, both EndoBI-1 and EndoBI-1 D184N showed a significant binding to these proteins compared to non-glycosylated controls (FIG. 6B).

E. Example 5: EndoBI-1 has Activity on Human Milk Glycoproteins

Figure 7A:
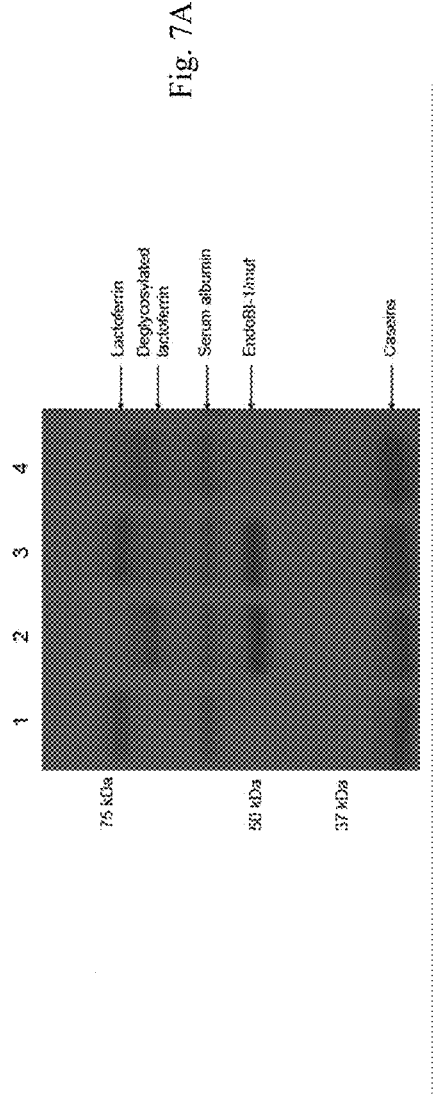
FIG. 7A-7B: EndoBI-1 activity in milk N-glycans. (A) SDS-PAGE gel of overnight incubation of human milk (lane 1, control) with EndoBI-1 (lane 2), EndoBI-1 D184N (lane 3) or PNGaseF (lane 4). (B) Amount of N-glycosylation (proportional to α-mannose) in samples from A. Error bars represent SD from triplicate experiments. Astrices represent samples with $p<0.05$ compared to control.
Figure 7B:
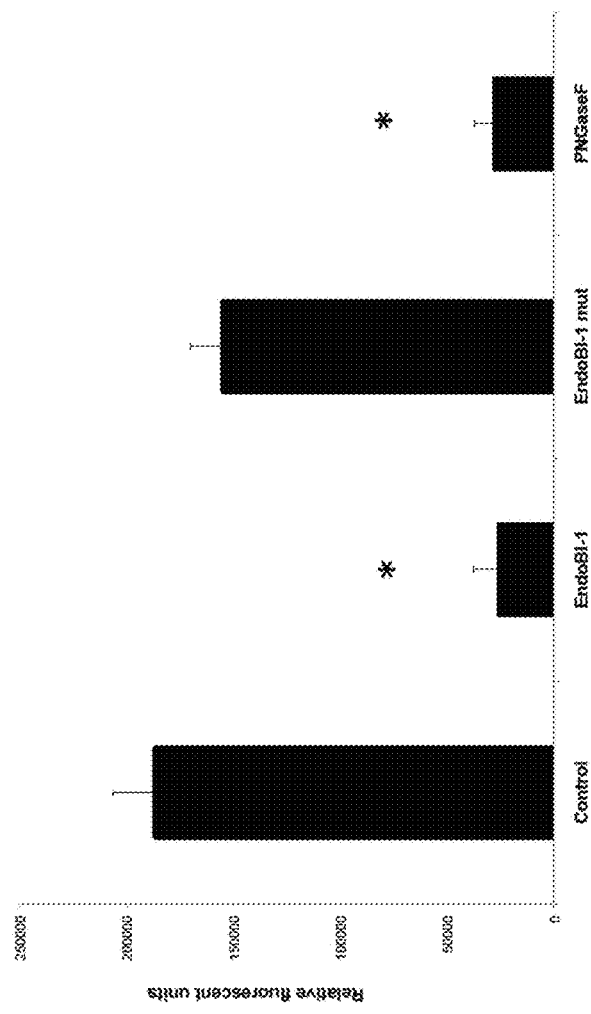

Breast milk is a complex fluid, characterized by diverse types and high amounts of N-linked, O-linked and non-glycosylated proteins. Overnight incubation of a fresh human milk sample with EndoBI-1 or PNGaseF produced a shift in the molecular weight of primarily lactoferrin (FIG. 7A). No change was observed when the milk sample was incubated with EndoBI-1 D184N. In a parallel experiment, the total amount of N-linked glycans, estimated as the amount of α-mannose detected by Concavalin A conjugated to FITC (ConA-FITC), was determined in digested milk samples. EndoBI-1 and PNGaseF, but not EndoBI D184N, significantly decreased the amount of α-mannose in breast milk (FIG. 7B), indicating extensive removal of N-linked glycans.

F. Example 6: Impact of hLF and bLF on B. infantis Gene Expression

Figure 8:
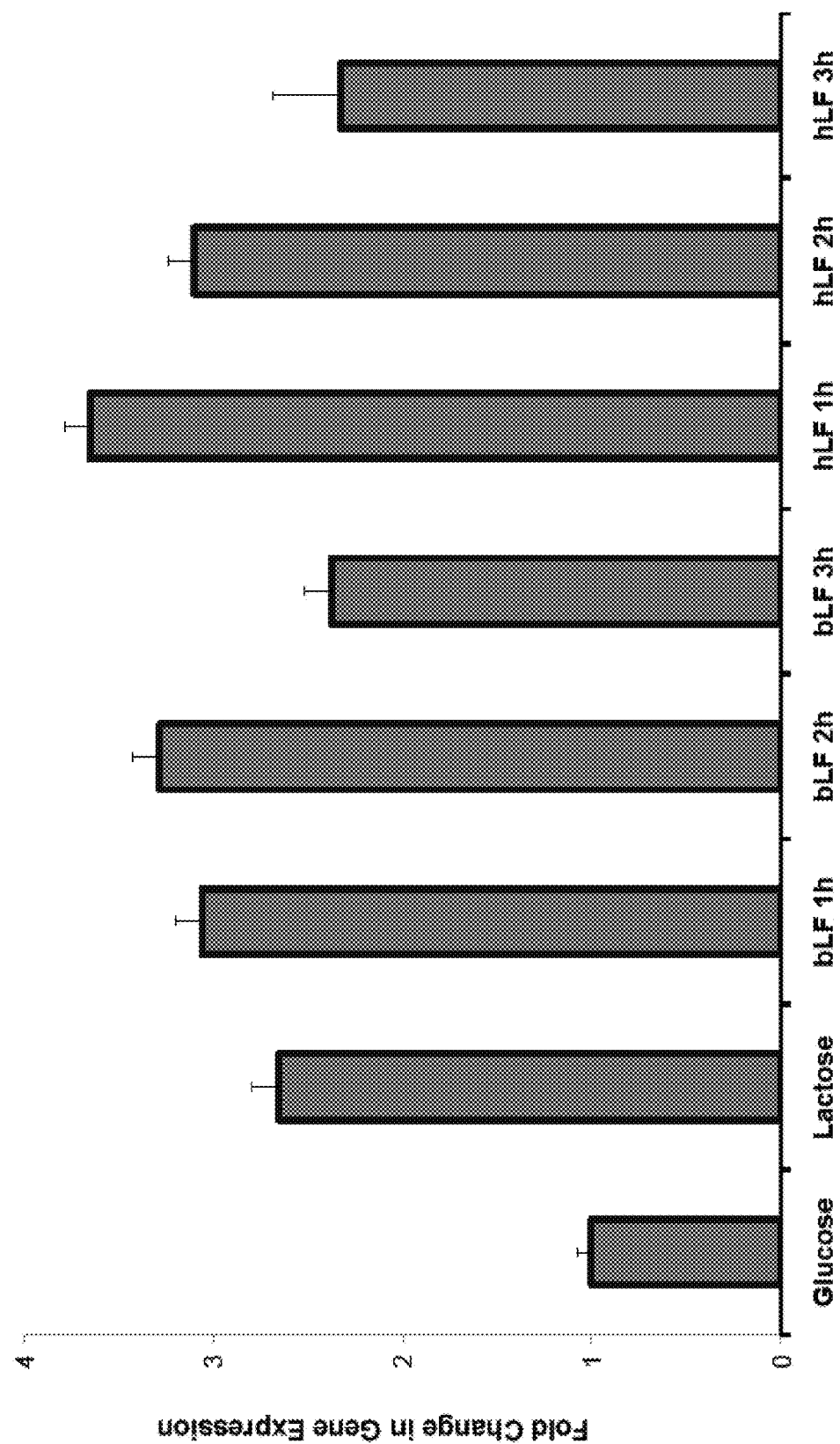
FIG. 8: Fold changes in gene expression of EndoBI-1 during time coincubation with bLF or hLF, as indicated in the figure legend. Locus tags are described in the text. Error bars represent SD from three biological replicates.
Figure 9A:
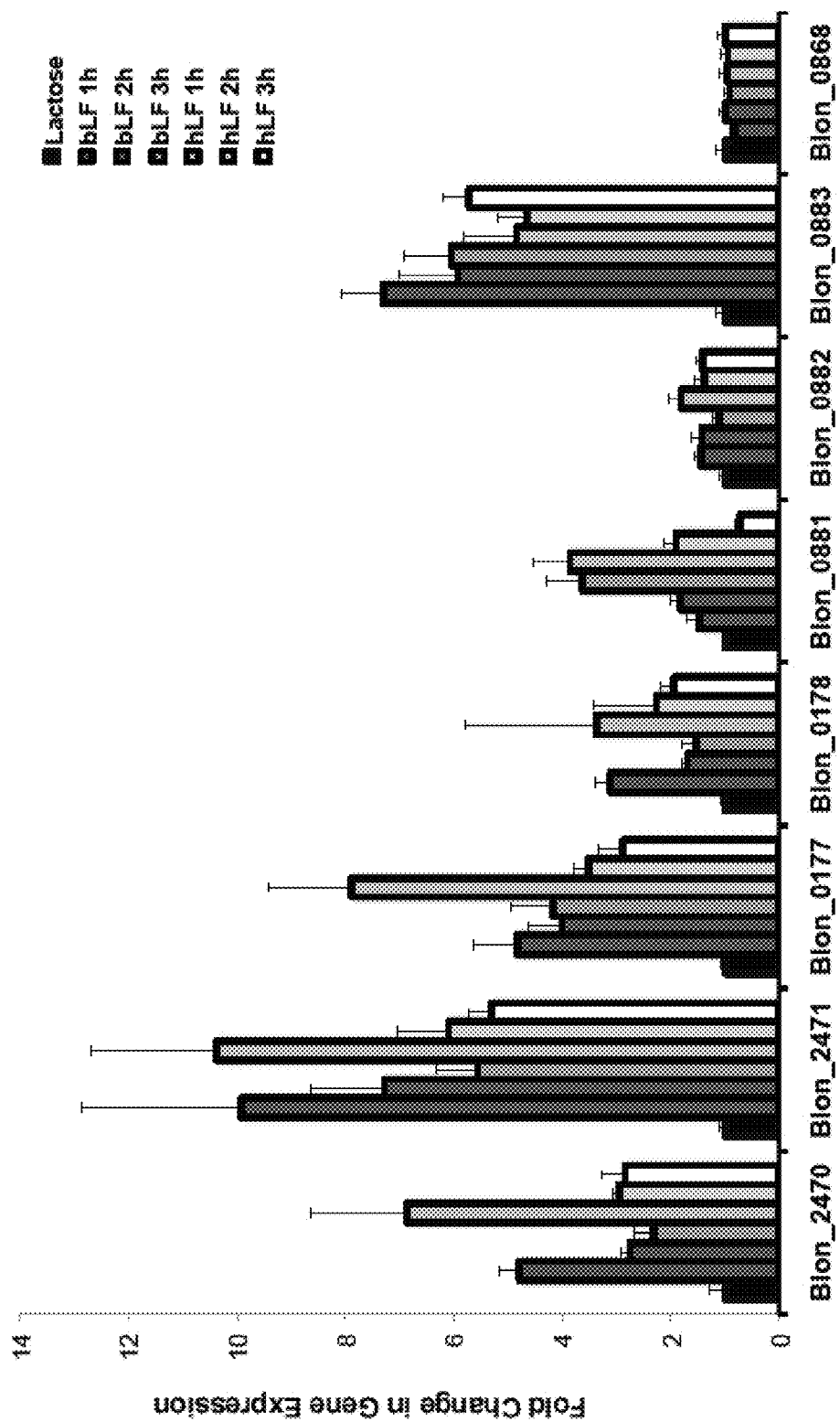
FIG. 9A-9B: Fold changes in gene expression for *B. infantis* ATCC 15697 genes during time coincubation with bLF or hLF, as indicated. Error bars represent SD from three biological replicates. (A) Genes associated to GlcNAc metabolism and located close to EndoBI-1. (B) Genes previously described to be associated or induced by human milk oligosaccharides (HMO).
Figure 9B:
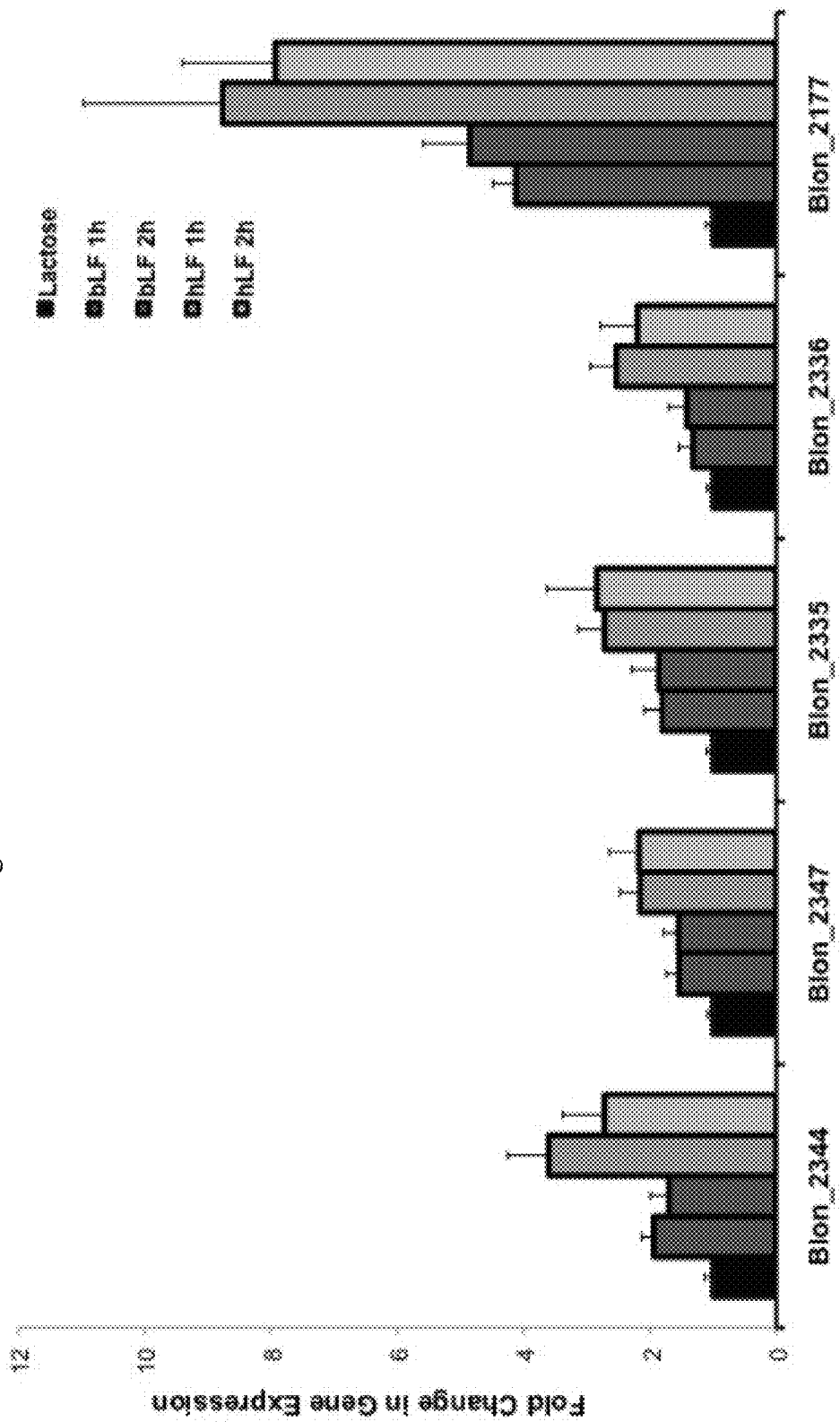

B. infantis ATCC 15697 in the presence of bLF or hLF revealed increased expression of Blon_2468 (EndoBI-1), compared to cells cultured with glucose. The level of expression was, however, similar to that from cells grown on lactose (FIG. 8). bLF and hLF each resulted in higher expression of other genes adjacent to Blon_2468 (EndoBI-1—see FIG. 2) including Blon_2470 and Blon_2471, encoding part of a PTS system specific for GlcNAc, (FIG. 9A). A similar trend was observed for Blon_0177 and Blon_0178, genes also associated to PTS systems in B. infantis. Other genes induced by these glycoproteins were Blon_0881 and to a lesser extent Blon_0882, key enzymes that participate in metabolism of GlcNAc and sialic acid. Putative genes in B. infantis associated to mannose metabolism (Blon_2380, solute binding protein for manno-oligosaccharides, and Blon_0868 and Blon_0869, α-mannosidases) were not affected by the presence of bLF or hLF. Conversely, several genes associated to the import and consumption of human milk oligosaccharides in B. infantis were significantly induced by hLF, and to a lesser extent bLF (FIG. 9B). In general the highest induction was observed after 1 hour. These genes included Blon_2344, Blon_2347, Blon_0883 and Blon_2177, solute-binding proteins that bind different classes of HMO associated to ABC transporters, as well as Blon_2335 and Blon_2336, two key fucosidases in the *B. infantis* genome.

G. Example 7: Utilization of Released Glycans

Figure 10:
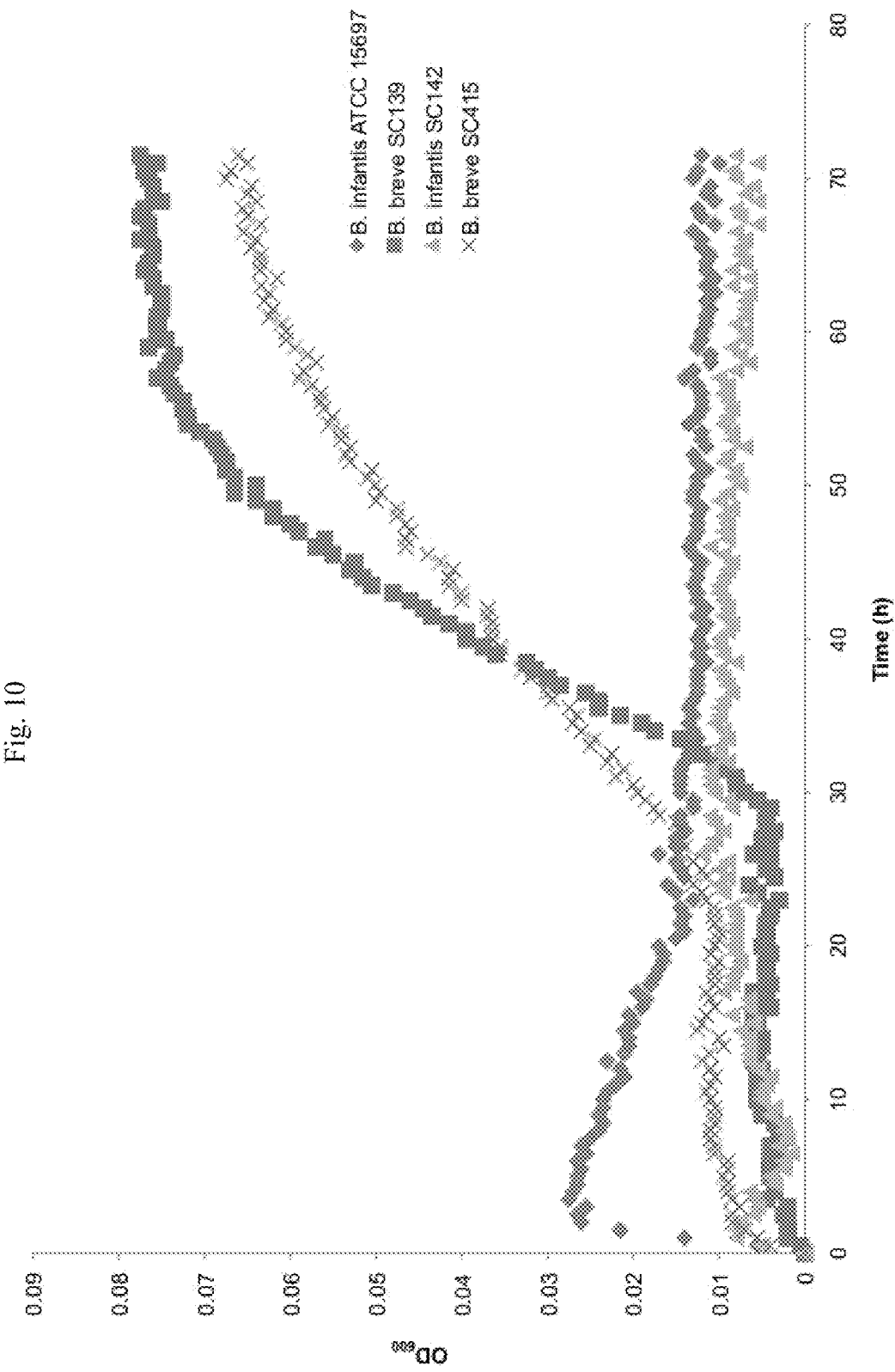
FIG. 10: Growth of bifidobacterial isolates on 10 mg/ml RNAseB. Lines are representative of three replicates.

GH18 enzyme-expressing bacteria such as *E. faecalis, S. pyogenes*, and *Capnocytophaga canimorsus* can use various glycoproteins as a carbon source. In addition, EndoS from *S. pyogenes*, specifically deglycosylates IgG, severely impairing immune reaction to the bacteria and increasing its survival in blood. *Bifidobacterium* isolates can grow well on N-linked glycans as a main carbon source. As shown in FIG. 10, *B. breve* KA179 and *B. breve* JCM7019 showed a minimal growth using 10 mg/ml of RNAseB.

H. Example 8: EndoBI-1 has Activity on Bovine Milk Glycoproteins

EndoBI-1, the GH18 enzyme expressed by *B. infantis* ATCC 15697 (Blon_2468), was tested for its activity on bovine milk glycoproteins using samples from a local dairy. The composition of released N-glycans was determined by Nano-LC (liquid chromatography) Q-TOF (quadrupole time-of-flight), and is shown in the tables below. N-glycans were characterized as follows:

Hex: Glucose, galactose, or mannose
Fuc: Fucose
NeuAc: N-acetylneuraminic acid
NeuGc: N-glycolylneuraminic acid Bovine Milk Sample 1

| Compound | Mass | Retention time | Volume (peak) | Hex | Fuc | HexNAc | NeuAc | NeuGc |
| --- | --- | --- | --- | --- | --- | --- | --- | --- |
| 1 | 1437.51 | 11.547 | 31856 | 5 | 0 | 3 | 0 | 0 |
| 2 | 1437.51 | 12.212 | 57092 | 5 | 0 | 3 | 0 | 0 |
| 3 | 1031.35 | 14.304 | 63882 | 5 | 0 | 1 | 0 | 0 |
| 4 | 1519.57 | 14.913 | 160198 | 3 | 0 | 5 | 0 | 0 |
| 5 | 1478.54 | 15.505 | 73266 | 4 | 0 | 4 | 0 | 0 |
| 6 | 1519.57 | 15.727 | 276803 | 3 | 0 | 5 | 0 | 0 |
| 7 | 1728.61 | 15.907 | 24540 | 5 | 0 | 3 | 1 | 0 |
| 8 | 1478.54 | 16.345 | 203480 | 4 | 0 | 4 | 0 | 0 |
| 9 | 1687.58 | 16.809 | 57655 | 6 | 0 | 2 | 1 | 0 |
| 10 | 1437.52 | 16.956 | 88016 | 5 | 0 | 3 | 0 | 0 |
| 11 | 1810.67 | 18.249 | 59921 | 3 | 0 | 5 | 1 | 0 |
| 12 | 1810.67 | 19.062 | 166554 | 3 | 0 | 5 | 1 | 0 |
| 13 | 1769.64 | 19.492 | 255565 | 4 | 0 | 4 | 1 | 0 |
| 14 | 1769.64 | 19.823 | 48888 | 4 | 0 | 4 | 1 | 0 |
| 15 | 1728.61 | 20.047 | 194087 | 5 | 0 | 3 | 1 | 0 |
| 16 | 1769.64 | 20.163 | 429713 | 4 | 0 | 4 | 1 | 0 |
| 17 | 1728.61 | 20.792 | 551414 | 5 | 0 | 3 | 1 | 0 |
| 18 | 1421.55 | 28.295 | 127956 | 4 | 1 | 3 | 0 | 0 |
| 19 | 1745.64 | 28.445 | 76358 | 6 | 1 | 3 | 0 | 0 |
| 20 | 1728.67 | 33.518 | 79818 | 5 | 0 | 3 | 1 | 0 |
| 21 | 1566.61 | 49.239 | 285443 | 4 | 0 | 3 | 1 | 0 |

Bovine Milk Sample 2

| Compound | Mass | Retention time | Volume (peak) | Hex | Fuc | HexNAc | NeuAc | NeuGc |
| --- | --- | --- | --- | --- | --- | --- | --- | --- |
| 1 | 1519.58 | 14.817 | 44196 | 3 | 0 | 5 | 0 | 0 |
| 2 | 1478.55 | 15.4 | 19365 | 4 | 0 | 4 | 0 | 0 |
| 3 | 1519.58 | 15.644 | 122126 | 3 | 0 | 5 | 0 | 0 |
| 4 | 1478.55 | 16.233 | 68580 | 4 | 0 | 4 | 0 | 0 |
| 5 | 1437.53 | 16.833 | 44391 | 5 | 0 | 3 | 0 | 0 |
| 6 | 1687.59 | 16.988 | 26907 | 6 | 0 | 2 | 1 | 0 |
| 7 | 1810.68 | 18.351 | 136099 | 3 | 0 | 5 | 1 | 0 |
| 8 | 1769.65 | 18.894 | 57851 | 4 | 0 | 4 | 1 | 0 |
| 9 | 1810.68 | 19.075 | 243243 | 3 | 0 | 5 | 1 | 0 |
| 10 | 1769.65 | 19.453 | 570306 | 4 | 0 | 4 | 1 | 0 |
| 11 | 1728.62 | 20.006 | 391845 | 5 | 0 | 3 | 1 | 0 |
| 12 | 1769.65 | 20.115 | 2E+06 | 4 | 0 | 4 | 1 | 0 |
| 13 | 1744.62 | 20.729 | 82204 | 5 | 0 | 3 | 0 | 1 |
| 14 | 1728.62 | 20.761 | 3E+06 | 5 | 0 | 3 | 1 | 0 |
| 15 | 1890.68 | 22.574 | 54025 | 5 | 1 | 3 | 0 | 1 |
| 16 | 1890.68 | 23.261 | 249499 | 5 | 1 | 3 | 0 | 1 |
| 17 | 1769.65 | 23.571 | 152940 | 4 | 0 | 4 | 1 | 0 |
| 18 | 2051.71 | 24.02 | 167688 | 5 | 0 | 3 | 0 | 2 |
| 19 | 2035.71 | 24.096 | 157601 | 5 | 0 | 3 | 1 | 1 |
| 20 | 2019.72 | 24.227 | 296020 | 5 | 0 | 3 | 2 | 0 |
| 21 | 2051.71 | 24.364 | 200140 | 5 | 0 | 3 | 0 | 2 |
| 22 | 2035.72 | 24.432 | 115802 | 5 | 0 | 3 | 1 | 1 |
| 23 | 2019.72 | 24.47 | 104626 | 5 | 0 | 3 | 2 | 0 |
| 24 | 2019.72 | 24.743 | 246864 | 5 | 0 | 3 | 2 | 0 |

The results show that the primary N-glycan produced in samples 1 and 2 comprises 5 Hex moieties, 3 HexNac moieties, and 1 NeuAc moiety (compounds 17 and 14, respectively). However, each of the free glycans produced by the deglycosylating enzyme can be used alone or in combination for prebiotic or probiotic compositions, e.g., to improve gut health or increase growth of bifidobacteria. The deglycosylation reaction results in a wealth of free glycans, as well as deglycosylated milk proteins that can be more easily digested. The results show that an enzyme produced by B. infantis can act on milk from multiple organisms to produce free glycans.

I. Summary

GH18 and GH85 endoglycosidases specifically cleave the N—N'-diacetylchitobiose core of N-linked glycans. EndoBI-1 and EndoBI-2 are representatives of two clades of GH18 sequences found in bifidobacteria (FIG. 1D). While their amino acid sequences are only 60% identical and possessed different gene contexts (FIG. 2), they shared a conserved active site, and acted on bovine and human lactoferrin.

The specificity of most known endoglycosidases is limited to high mannose glycans (e.g., EndoH). EndoS acts solely on IgG. Endoglycosidases F1, F2 and F3 show a preference for either high mannose or complex oligosaccharides, but not both. In contrast, EndoBI-1 showed broad substrate specificity, releasing N-glycans from human IgA, IgG, RNase B and bovine fetuin, as well as human milk (FIGS. 4, 5, and 7). Each one of these proteins has a unique type of N-glycosylation, suggesting that EndoBI-1 can cleave high mannose, hybrid or complex N-glycans containing core α1-6 fucosylation, polylactosamine α1-3 fucosylation, and terminal sialylation.

The presently disclosed deglycosylating enzymes retained activity after incubation at 95° C. for 5 minutes. This property allows for the denaturing of glycoprotein substrate for greater access to glycosylated sites, and higher activity. In addition, Bifidobacteria are already designated GRAS by the FDA, so the enzymes can be recombinantly expressed in these bacteria for probiotic applications. Unlike PNGaseF, EndoBI-1 leaves a residual GlcNAc attached to the asparagine of the protein, which can be useful for glycosite determination in glycoproteomic applications.

Several bifidobacteria in this study possessed a GH85 enzyme. EndoBB (BLD_0197) from B. longum DJO10A cleaved high mannose glycans, cleaving RNAseB and bLF, but not hLF. The function of GH85 endoglycosidases in these B. breve isolates may be associated to β-galactosidases, β-hexosaminidases and α-sialidases. The presence of α-mannosidases and an ABC importer for oligosaccharides near these genes indicate related function, and that these clusters may be active on plant-derived oligosaccharides.

Endoglycosidase EndoBI-1 in B. infantis ATCC 15697 was constitutively expressed during coincubation with bovine and human lactoferrin. Strains of B. infantis can use HMO as a sole carbon source (Locascio et al., Microb Biotechnol 2:333-342 (2009)). Genes induced by HMO in B. infantis, such as solute binding proteins and α-fucosidases (Garrido et al., PLoS One 6:e17315 (2011); Sela et al., Applied and Environmental Microbiology (2011)), were also up-regulated by hLF and bLF (FIG. 9), suggesting that bacterial responses to these milk components are in part coregulated.

J. Materials and Methods

Bacteria and Media.

Bifidobacterium strains used in this study are listed in Table 4. For routine experiments, bifidobacteria were grown on de Mann-Rogose-Sharp broth with no carbon source (mMRS), supplemented with 0.05% w/v L-cysteine (Sigma-Aldrich, St. Louis, Mo.) and 2% lactose. Zhang-Mills-Block (ZMB-1) media was used for evaluation of bacterial growth on glycoproteins or transcriptional analyses. Cells were anaerobically grown in a vinyl chamber (Coy Laboratory Products, Grass Lake, Mich.) at 37° C. for 24 h. Competent Escherichia coli BL21 Star and Top10 cells were from Invitrogen (Carlsbad, Calif.). Transformant E. coli cells were grown in Luria Broth with 50 µg/ml Carbenicillin (Teknova, Hollister Calif.) when necessary at 37° C.

Incubations of Bifidobacteria with Glycoproteins.

Bifidobacterial isolates were grown on 2 ml mMRS with 2% lactose to mid-late exponential phase. Cultures were centrifuged for 1 min at 12000 rpm, and resuspended in 2 ml of mMRS supplemented with 5 mg/ml of ribonuclease B from bovine pancreas (Sigma-Aldrich, St. Louis, Mo.). Incubations were run for 18 hours, and supernatants were recovered after centrifugation 1 min at 12000 rpm. A 1:10 dilution of each supernatant was denatured in glycoprotein denaturing buffer (0.5% SDS and 40 mM DTT) and analyzed on 4-15% precast SDS-PAGE gels (Bio-Rad, Carlsbad Calif.). Growth of specific bacteria was also analyzed on 96 well plates containing 200 µl of ZMB-1 media and 10 mg/ml of RNAseB, or 5 mg/ml of lactoferrin from human milk (Sigma) and lactoferrin from bovine milk (Sigma). Cultures were inoculated at 2% and grown for 72 h in a PowerWave microplate reader (BioTek Instruments, Inc., Winoosky, Vt.), under anaerobic conditions. Growth was monitored using GenS 1.10 (BioTek). Cultures were grown in triplicate, and controls containing no glycoprotein and no bacteria were included and subtracted from OD600 values.

Endoglycosidase Sequence Determinations.

Protein coding sequences belonging to GH18 found in the genomes in B. infantis ATCC 15697 (Blon_2468), B. infantis 157F (BLIF_1310, and Enterococcus faecalis OG1RF (EndoEα) were aligned using MUSCLE. Conserved regions were selected and converted to DNA to design degenerate primers (Table S2). A similar approach was used with sequences encoding GH85 enzymes, found in the published genome sequences of B. longum DJO10A (BLD_0197), B. longum NCC2703 (BL1335) and B. breve UCC2003.

Genomic DNA was prepared from overnight cultures on MRS for each strain used in this study using the DNeasy Blood & Tissue Kit (Qiagen, Valencia Calif.). 50 µl PCR reactions contained 1 U of Phusion DNA polymerase (Finnzymes, Vantaa, Finland), 1 ng of DNA, 0.2 mM of dNTPs and 0.5 µM of each degenerate primers (Table S2), and were run in a PTC200 Thermo Cycler (MJ Research, Ramsey, Minn.). The PCR program included an initial denaturation at 98° C. for 2 min, 30 cycles of denaturation at 98° C. 30 s, annealing at 55° C. for 90 s, extension at 72° C. 2 min, and a final extension at 72° C. for 7 min. PCR products were purified using the Qiaquick PCR product purification kit (Qiagen), and sequenced at the UC Davis DNA sequencing facility. GH18 sequences were analyzed using BioEdit 7.1.3, and later expanded and fully determined using the DNA Walking SpeedUp Premix Kit (Seegene, Rockville Md.), and the TSP142 primers listed in Table 3. GH85 sequences were directly determined using primers GH85cF and GH85cR.

Bioinformatic Analyses.

The Integrated Microbial Genomes (IMG) (Markowitz et al. (2006) Nuc. Acid Res. 34:344-388) database was used to find GH18 and GH85 protein sequences in Bifidobacterium genomes and to determine genetic landscapes for GH18-type and GH85-type genes found in the genomes of *B. infantis* ATCC 15697, *B. infantis* 157F and *B. longum* DJO10A. Multiple sequence alignments were performed using MUSCLE, using the Maximum Likelihood algorithm in MEGA v 5.0.

Gene Cloning and Expression.

Genomic DNA from *B. infantis* ATCC 15697, *B. infantis* SC142 and *B. longum* DJO10A was amplified with the cloning primers indicated in Table 3, targeting GH18 or GH85 sequences. Signal peptides and transmembrane domains were omitted in this amplification to facilitate protein expression in, and purification from, *E. coli*. PCR reactions contained 0.5 µM of each primer, 1 ng DNA, 0.2 mM dNTPs (Fermentas, Glen Burnie, Md.), and 2 U of Phusion DNA Polymerase (Finnzymes, Vantaa, Finland) in a 150 µl final volume. PCR was performed in a PTC200 Thermo Cycler, using the following program: initial denaturation at 98° C. for 2 min, 35 cycles of denaturation at 98° C. 30 s, annealing at 58° C. for 90 s, extension at 72° C. 2 min, and a final extension at 72° C. for 7 min. PCR products were gel-purified (Qiaquick Gel Extraction Kit, Qiagen). Induction was performed with 0.5 mM IPTG at 28° C. (EndoBI-1, EndoBI-2 and EndoBI-1mut), or with 1 mM IPTG at 37° C. (EndoBB). Proteins were concentrated using Amicon Ultra 30 kDa 4 ml columns, and buffer was exchanged for saline sodium citrate 1× using Bio-Gel P-30 in SSC Buffer columns.

Glycoprotein Digestion by Bifidobacterial Endoglycosidases.

Optimal reaction conditions for endoglycosidases EndoBI-1, EndoBI-2 and EndoBB were determined by incubation with RNAseB. Reactions were performed in a 10 µl volume and included 4 µg of RNAse B, 1 µg of each enzyme and 4 µl of 0.2 M $Na_2HPO_4$ with pH values between 5.0 and 7.0 at 37° C. Reactions were run for 1 h, stopped with 1 M $Na_2CO_3$, treated with the denaturing buffer as above and loaded into 4-15% precast polyacrylamide SDS gels. Optimum temperature reaction was determined at each respective optimum pH, and reactions were performed at 4°, 30°, 37°, 45°, 55° and 65° C. for 1 h. Heat resistance was evaluated by incubating each glycosidase at 95° C. for 1, 5 and 30 min, and enzyme reactions were then carried out under optimal conditions. Digestions of human and bovine lactoferrin (Sigma) were performed under optimal conditions using 4 µg of each glycoprotein and incubated for 18 h with 1 µg of each endoglycosidase, or 1 µl of glycerol-free peptide:N-glycosidase F (PNGaseF 500 U/µl; New England Biolabs, Ipswich, Mass.). Finally 20 µl of a fresh breast milk sample in 20 mM $Na_2HPO_4$ pH 5.0 were incubated for 18 h with 10 µg of EndoBI-1, 10 µg of EndoBI-1 mut or 1 µl of PNGaseF under optimal conditions. Lactoferrin and human milk digestions were evaluated in 7.5% precast SDS-PAGE gels under denaturing conditions. All experiments were performed at least in duplicates.

Mass Spectrometry

Site Directed Mutagenesis.

A plasmid containing Blon_2468 (with signal sequence and transmembrane domains deleted) was resynthesized with mutagenic primers AmpR and 2468mutF (Table S2) using the Change-IT multiple mutation site directed mutagenesis kit (USB Corporation, Santa Clara Calif.) and following manufacturer instructions. Mutated plasmids were cloned into Top10 competent cells (Invitrogen), and after verifying the proper mutation were transformed into BL21 competent cells. EndoBI-1mut was purified as described in the previous section, with induction carried on with 0.5 mM IPTG at 28° C. for 6 h.

Glycan Array Analysis.

Purified EndoBI-1 D184N (100 µg/ml, 200 µl), was analyzed for glycan binding by the Consortium for Functional Glycomics using the Mammalian Printed Array v5.0. Protocols are available at the website of functionalglycomics.org. Detection was performed using an Anti-His-FITC antibody (Invitrogen).

*B. infantis* gene expression. *B. infantis* cells were grown on ZMB-1 media with 2% lactose as describe above. Six ml of an exponential culture ($OD_{405}$ 0.8-1) were centrifuged for 1 min at 12000×g, and immediately resuspended in 5 ml of prewarmed ZMB-1 supplemented with either human lactoferrin or bovine lactoferrin (5 mg/ml). Cultures were rapidly returned to anaerobic conditions, and 1 ml of each culture was taken anaerobically every hour. One ml of the original culture grown on lactose (t=0), and hourly time points of incubations with bLF or hLF (t=1-3 h), were centrifuged at 12000×g for 1 min, and the pellet was resuspended in 1 ml of RNAlater (Ambion, Austin, Tex.). The experiment was done in duplicate. Cell suspensions were stored overnight at 4° C. and then at −80° C. until use. RNA extraction, quality check and cDNA conversion were performed as in Garrido et al. (2011) *PLoS One* e17315. Relative quantification for genes listed in Table 3 was performed in a 7500 Fast Real-Time PCR System (Applied Biosystems, Foster City, Calif.) and using the Fast Sybr Green Master Mix (Applied Biosystems). Reaction conditions were as recommended by manufacturer using 0.5 µM of each primer. Primers for qPCR were designed using the NCBI primer design tool, checking for specificity along the *B. infantis* ATCC 15697 genome (Table 3).

Fluorescence Assays.

Binding of EndoBI-1 and EndoBI-1 D184N to glycoproteins was determined after overnight coating in microtiter 96 well plates of 20 µmoles of RNAseB, bLF, hLF or BSA in PBS buffer at room temperature. The experiment was performed in triplicate. Wells were washed with PBS three times, and blocked after incubation with BSA 3% at RT for 1 h. Ten µmoles of EndoBI-1, EndoBI-1 D184N and BSA were added to the wells and incubated for 2 h at 37° C. in PBS buffer adjusted to pH 5.0. Wells were washed three times with PBS-Tween 20 0.05%, and incubated for 1 h with a 1:500 dilution of FITC-Anti-His (C-term) antibody (Invitrogen). After 4 washes with PBS-Tween, fluorescence was monitored in a Synergy2 Microplate reader (Biotek), at 485/530 nm emission/excitation. In another set of experiments, fresh milk samples incubated overnight with EndoBI-1, EndoBI-1 D184N or PNGaseF as described above were coated overnight in a microtiter 96-well plate. After washing three times with PBS buffer, wells were incubated with a 1:500 dilution of 5 mg/ml of fluorescein labeled Concavalin A (Vector labs, Burlingame Calif.) for 1 h at 37° C. Wells were washed four times with PBS-Tween 20 0.05%, and fluorescence was read as described above. Experiment was repeated twice.

TABLE 1

Alignment of extracellular domain subsequences for GH18 enzymes (SEQ ID NOs: 7-20)

| | | | |
|---|---|---|---|
| B. infantis ATCC 15697 | 150 | TESEATEADYDAYAKQVIDKYMISVGLDGLDIDMEAHPNDADVKISDNVI(EndoBI-1) | 199 |
| B. infantis ATCC 15702 | 150 | TESEATEADYDAYAKQVIDKYMISVGLDGLDIDMEAHPNDADVKISDNVI | 199 |
| B. infantis ATCC 17930 | 150 | TESEATEADYDAYAKQVIDKYMISVGLDGLDIDMEAHPNDADVKISDNVI | 199 |
| B. infantis JCM11346 | 150 | TESEATEADYDAYAKQVIDKYMISVGLDGLDIDMEAHPNDADVKISDNVI | 199 |
| B. infantis JCM7007 | 150 | TESEATEADYDAYAKQVIDKYMISVGLDGLDIDMEAHPNDADVKISDNVI | 199 |
| B. infantis JCM7009 | 150 | TESEATEADYDAYAKQVIDKYMISVGLDGLDIDMEAHPNDADVKISDNVI | 199 |
| B. infantis JCM7011 | 150 | TESEATEADYDAYAKQVIDKYMISVGLDGLDIDMEAHPNDADVKISDNVI | 199 |
| B. infantis 157F | 120 | NVDSATESDYDAYADHVIETYMTSVGLDGLDIDMETFPDAAQVAISDQVI | 169 |
| B. infantis SC142 | 120 | NVDSATESDYDAYADHVIETYMTSVGLDGLDIDMETFPDAAQVAISDQVI(EndoBI-2) | 169 |
| B. infantis SC143 | 120 | NVDSATESDYDAYADHVIETYMTSVGLDGLDIDMETFPDAAQVAISDQVI | 169 |
| B. longum SC116 | 120 | NVDSATESDYDAYADHVIETYMTSVGLDGLDIDMETFPDAAQVAISDQVI | 169 |
| B. longum SC630 | 120 | NVDSATESDYDAYADHVIETYMTSVGLDGLDIDMETFPDAAQVAISDQVI | 169 |
| B. longum SC706 | 120 | NVDSATESDYDAYADHVIETYMTSVGLDGLDIDMETFPDAAQVAISDQVI | 169 |
| EndoE | 152 | AGTTPTEAEFDAYAKELLTKFVDDLGID<u>GLDIDME</u>TRPSEKDIVLSNGVI | 201 |

TABLE 2

Alignment of extracellular domain subsequences for GH85 enzymes (SEQ ID NOs: 21-31)

| | | | |
|---|---|---|---|
| B. breve SC95 | 150 | SDGSFPVADKLIEVATTYGFDGWFINQETEGENETSLGADYATKMQAFIAYLKK | 199 |
| B. breve JCM1273 | 150 | SDGSFPVADKLIEVATTYGFDGWFINQETEGENETSLGADYATKMQAFIAYLKK | 199 |
| B. breve JCM7019 | 150 | SDGSFPVADKLIEVATTYGFDGWFINQETEGENETSLGADYATKMQAFIAYLKK | 199 |
| B. breve JCM7020 | 150 | SDGSFPVADKLIEVATTYGFDGWFINQETEGENETSLGADYATKMQAFIAYLKK | 199 |
| B. breve KA179 | 150 | SDGSFPVADKLIEVATTYGFDGWFINQETEGENETSLGADYATKMQAFIAYLKK | 199 |
| B. breve SC139 | 150 | SDGSFPVADKLIEVATTYGFDGWFINQETEGENETSLGADYATKMQAFIAYLKK | 199 |
| B. breve SC506 | 150 | SDGSFPVADKLIEVATTYGFDGWFINQETEGENETSLGADYATKMQAFIAYLKK | 199 |
| B. breve SC568 | 120 | SDGSFPVADKLIEVATTYGFDGWFINQETEGENETSLGADYATKMQAFIAYLKK | 169 |
| B. longum DJO10A | 120 | SDGSFPVADKLIEVATTYGFDGWFINQETEGENETSLGADYATKMQAFIAYLKK (EndoBB) | 169 |
| B. breve UCC2003 | 120 | SDGSFPVADKLIEVATTYGFDGWFINQETEGENETSLGADYATKMQAFIAYLKK | 169 |
| EndoD | 287 | ADGSFPIARKLVDMAKYYGYDGY<u>FINQET</u>TGDLVKPLGE----KMRQFMLYSKE | 336 |

TABLE 3

Primers

| Primer name | Primer sequence (5'-3') |
|---|---|
| a) Degenerate primers (SEQ ID NOs: 32-35) | |
| GH85degF | TAYTGGCARTAYGTNGAY |
| GH85degr | CCAYTTYTCRTCRTCYTC |
| GH18degF | CTNGAYATHGAYATGGAR |
| GH18degR | NGANCCRTAYTGYTGRTA |
| b) DNA walking (SEQ ID NOs: 36-41) | |
| TSP142-5F1 | CAACCGAGGTCATGTACGTT |
| TSP142-5F2 | CGTAATCGCTCTTGAGCTTGTC |
| TSP142-5F3 | ACTGGGAACGTAGCTGAACA |
| TSP142-5R1 | AACGTACATGACCTCGGTTG |

TABLE 3-continued

Primers

| Primer name | Primer sequence (5'-3') |
|---|---|
| TSP142-5R2 | CACGATGTTCCTTTACGACACC |
| TSP142-5R3 | GACACCAATGGCAGCTACACTG | c) Cloning of bifidobacterial endoglycosidases (SEQ ID NOs: 42-47)

| | |
|---|---|
| 2468F11 | CACCATGAATGCGGACGCCGTTTCTCCGAC |
| 2468R11 | GCCGGTCGCACTCAGTTGCTTCGG |
| 142cF | CACCATGGTTGCGAACGCCCAGGAGGGGGA |
| 142cR | CGCCGCGTTTCTGGCCGTGGTCA |
| GH85cF | CACCATGACCAAGTACACGATCACACCGGAG |
| GH85cR | GGTACGTGGCGCAGACGGCGCGATCCTC | d) Site directed mutagenesis (SEQ ID NO: 48)

| | |
|---|---|
| 2468mutP | (PO4)-GATATCGACATGCAGGCGCACCCGAAT | e) qPCR (SEQ ID NOs: 49-72)

| | |
|---|---|
| Blon0393qF | TTCACCGAGGCGTACAACA |
| Blon0393qR | CGCATCCGTGACCACATAG |
| Blon2468qF | ACAGAGCCACCCCTGCGATG |
| Blon2468qR | GCCGGTTCCGACGCCAGATT |
| Blon2470qF | CACGATGCTGGTGAGTGC |
| Blon2470qR | CCGGAACCGGTAAGATCC |
| Blon2471qF | ACAACCGTTTCAGCAAGACC |
| Blon2471qR | GAGCAGACGGTTGAAGAAGG |
| Blon2472qF | ATGATCGCCGTCACGATATT |
| Blon2472qR | GAACATCAGCAGGGAGAAGC |
| Blon0177qF | TCCGGTCGGCATTCACGCAC |
| Blon0177qR | GGCAACGGTCTCGGCGTTGT |
| Blon0178qF | TGGTCTGCGCACGCTGAAGG |
| Blon0178qR | GGCACCTCGGCCATCACACC |
| Blon0881qF | GGCCACGTCGGCTTCAACGA |
| Blon0881qR | GAACGCCAGCAGCACGAGGT |
| Blon0882qF | TCGTTTCCCGCGTGACCACG |
| Blon0882qR | CCACGTAGCCGGGGGTCAGA |
| Blon0883qF | ATCGAAGCCGTGTGGATT |
| Blon0883qR | CCTCGTTGTAGGCGTCGTA |
| Blon0868qF | ACAGCTCGCGGTGGAGTCCT |
| Blon0868qR | TCCAGCGGCTTGCCTTTCGG |
| Blon0869qF | GCAGCAGCGTGTCAAACCGC |
| Blon0869qR | GCCGGGAACGCGGAAAGGTT |
| Blon2335qF | CCTGTTCAACCAGGATGAGTC |
| Blon2335qR | CCGTCCACGACGAAGTAG |
| Blon2336qF | ATCACGCTCACCCTCCC |
| Blon2336qR | ACATCGTCGAAGCGGAGT |
| Blon2177qF | GGTTCCTGAGGTCTTCACCA |
| Blon2177qR | GCCGAGCTTCTCAAATTCA |
| Blon2344qF | TCAAGAAGCTCGACCCGTTG |
| Blon2344qR | TTGGCGTAGAAGCCGTATGT |
| Blon2347qF | AAGCCGATAGGTTCTCCCT |
| Blon2347qR | TCGCCTTGGTGTACTTGTCT |

TABLE 4

Bacterial strains

| Code | Identification | Additional strain information | Source | GH gene present¶ | Endoglycosidase activity§ |
|---|---|---|---|---|---|
| ATCC15697 | *B. longum* subsp. *infantis* | JCM1222; DSM20088 | Intestine of infant | GH18a | Yes |
| ATCC25962 | *B. longum* subsp. *infantis* | JCM1210; DSM20223 | Intestine of infant | — | No |
| ATCC17930 | *B. longum* subsp. *infantis* | JCM1260; DSM20218 | Infant feces | GH18a | Yes |
| ATCC15702 | *B. longum* subsp. *infantis* | JCM1272; DSM20090 | Intestine of infant | GH18a | Yes |
| JCM7007 | *B. longum* subsp. *infantis* | LMG18901 | Infant feces | GH18a | Yes |
| JCM7009 | *B. longum* subsp. *infantis* | LMG18902 | Infant feces | GH18a | No |

TABLE 4-continued

| | | Bacterial strains | | | |
|---|---|---|---|---|---|
| Code | Identification | Additional strain information | Source | GH gene present¶ | Endoglycosidase activity§ |
| JCM7011 | *B. longum* subsp. *infantis* | | Infant feces | GH18a | No |
| JCM11346 | *B. longum* subsp. *infantis* | Isolates | Infant feces | GH18a | No |
| 157F | *B. longum* subsp. *infantis* | | Infant feces | GH18b | ND |
| SC30 | *B. longum* subsp. *infantis* | Isolates | Infant feces | — | ND |
| SC97 | *B. longum* subsp. *infantis* | Isolates | Infant feces | — | ND |
| SC117 | *B. longum* subsp. *infantis* | Isolates | Infant feces | — | ND |
| SC142 | *B. longum* subsp. *infantis* | Isolates | Infant feces | GH18b | Yes |
| SC143 | *B. longum* subsp. *infantis* | Isolates | Infant feces | GH18b | Yes |
| SC145 | *B. longum* subsp. *infantis* | Isolates | Infant feces | — | ND |
| SC268 | *B. longum* subsp. *infantis* | Isolates | Infant feces | — | ND |
| SC417 | *B. longum* subsp. *infantis* | Isolates | Infant feces | — | ND |
| SC523 | *B. longum* subsp. *infantis* | Isolates | Infant feces | — | ND |
| SC569 | *B. longum* subsp. *infantis* | Isolates | Infant feces | — | ND |
| SC600 | *B. longum* subsp. *infantis* | Isolates | Infant feces | — | ND |
| SC605 | *B. longum* subsp. *infantis* | Isolates | Infant feces | — | ND |
| SC638 | *B. longum* subsp. *infantis* | Isolates | Infant feces | — | ND |
| SC638 | *B. longum* subsp. *infantis* | Isolates | Infant feces | — | ND |
| DJO10A | *B. longum* subsp. *longum* | Isolates | Infant feces | GH85 | Yes |
| SC91 | *B. longum* subsp. *longum* | Isolates | Infant feces | — | No |
| SC116 | *B. longum* subsp. *longum* | Isolates | Infant feces | GH18b | Yes |
| SC156 | *B. longum* subsp. *longum* | Isolates | Infant feces | — | No |
| SC215 | *B. longum* subsp. *longum* | Isolates | Infant feces | — | ND |
| SC249 | *B. longum* subsp. *longum* | Isolates | Infant feces | — | ND |
| SC280 | *B. longum* subsp. *longum* | Isolates | Infant feces | — | ND |
| SC513 | *B. longum* subsp. *longum* | Isolates | Infant feces | — | ND |
| SC536 | *B. longum* subsp. *longum* | Isolates | Infant feces | — | ND |
| SC558 | *B. longum* subsp. *longum* | Isolates | Infant feces | — | No |
| SC592 | *B. longum* subsp. *longum* | Isolates | Infant feces | — | ND |
| SC596 | *B. longum* subsp. *longum* | Isolates | Infant feces | — | ND |
| SC618 | *B. longum* subsp. *longum* | Isolates | Infant feces | — | No |
| SC630 | *B. longum* subsp. *longum* | Isolates | Infant feces | GH18b | Yes |
| SC633 | *B. longum* subsp. *longum* | Isolates | Infant feces | — | ND |
| SC657 | *B. longum* subsp. *longum* | Isolates | Infant feces | — | ND |
| SC662 | *B. longum* subsp. *longum* | Isolates | Infant feces | — | ND |
| SC700 | *B. longum* subsp. *longum* | Isolates | Infant feces | — | ND |
| SC706 | *B. longum* subsp. *longum* | Isolates | Infant feces | GH18b | Yes |
| UCC2003 | *B. breve* | Isolates | Infant nursing stool | GH85 | ND |

TABLE 4-continued

Bacterial strains

| Code | Identification | Additional strain information | Source | GH gene present¶ | Endoglycosidase activity§ |
|---|---|---|---|---|---|
| ATCC15698 | B. breve | JCM1273; DSM20091 | Intestine of infant | GH85 | Yes |
| ATCC15700 | B. breve | JCM1192; DSM20213 | Intestine of infant | — | No |
| ATCC15701 | B. breve | JCM7016 | Intestine of infant | — | No |
| JCM7017 | B. breve | | Human feces | — | No |
| JCM7019 | B. breve | | Infant feces | GH85 | Yes |
| JCM7020 | B. breve | | Infant feces | GH85 | Yes |
| S-17c | B. breve | Roy et al. 1996 (Int. J. Food Microbiol., 29, 11-29 | Infant feces | — | No |
| S-46 | B. breve | Roy et al. 1996 (Int. J. Food Microbiol., 29, 11-29 | Infant feces | — | No |
| SC81 | B. breve | Isolates | Infant feces | — | No |
| SC95 | B. breve | Isolates | Infant feces | GH85 | Yes |
| SC139 | B. breve | Isolates | Infant feces | GH85 | Yes |
| SC154 | B. breve | Isolates | Infant feces | — | No |
| SC500 | B. breve | Isolates | Infant feces | — | ND |
| SC506 | B. breve | Isolates | Infant feces | GH85 | Yes |
| SC522 | B. breve | Isolates | Infant feces | — | No |
| SC559 | B. breve | Isolates | Infant feces | | Yes |
| SC567 | B. breve | Isolates | Infant feces | — | No |
| SC568 | B. breve | Isolates | Infant feces | GH85 | Yes |
| SC573 | B. breve | Isolates | Infant feces | — | No |
| SC580 | B. breve | Isolates | Infant feces | — | No |
| KA179 | B. breve | Isolates | Infant feces | GH85 | Yes |
| JCM1254 | B. bifidum | DSM20082 | Intestine of adult | — | No |
| ATCC29521 | B. bifidum | JCM1255; DSM20456 | Infant feces | — | No |
| ATCC11863 | B. bifidum | JCM1209; DSM20082 | | — | No |
| JCM7002 | B. bifidum | | Human feces | — | No |
| JCM7003 | B. bifidum | | Human feces | — | No |
| JCM7004 | B. bifidum | | Intestine of infant | — | No |
| ATCC29521 | B. bifidum | JCM1255 | Infant feces | — | No |
| KA75 | B. bifidum | Starter culture | Probioplus | — | No |
| SC112 | B. bifidum | Isolates | Infant feces | — | No |
| SC126 | B. bifidum | Isolates | Infant feces | — | No |
| SC555 | B. bifidum | Isolates | Infant feces | — | No |
| SC572 | B. bifidum | Isolates | Infant feces | — | No |
| SC583 | B. bifidum | Isolates | Infant feces | — | No |

VIII. Informal Sequence Listing

```
Active site for GH18 enzymes
                                       SEQ ID NO: 1
GLDIDME Active site for GH85 enzymes
                                       SEQ ID NO: 2
FINQET Full length EndoBI-1 (Blon_2468 from B. infantis
ATCC 15697)
Signal sequences underlined and transmembrane
domains italicized
                                       SEQ ID NO: 3
MTFIKQMMPRYVASMTAGIVAAAMAATCAFAPVANADAVSPTQETIQSTG

RHFMVYYRAWRDVTMKGVNTDLPDDNWISMYDIPYGVDVVNIFSYVPSGQ

EEQAQPFYDKLKSDYAPYLHSRGIKLVRGIDYTGVAVNGFRTFMKEQNKT

ESEATEADYDAYAKQVIDKYMISVGLDGLDIDMEAHPNDADVKISDNVIR

ALSKHIGPKSAKPDTTMELYDINGSYLNPFKNVAECFDYVAYQQYGSSSD

RTARAAADYQPYIGNEFVPGLTFPEEGDMNNRWYDATEPYEESHFYQVAS

YVREHNLGGMFVYALDRDGRNYDEDLRRIVPSNLLWTKTAIAESEGMALD

TAKTAANHYLDRMSLRQVIDDNAASADKARDMVGKAANLYETNKAVLGGD

YGEGFSNTYDPTLEAGLLGIDISVLQQQIDKSSEIIGADTAESDAKTALR

MARDAAIDGLTGKIYTADQVSAWSQALKAALDATVPVPTPDSTDQNGNRD

KVTNHKVQGQPKQLSATGISTDIIVAVGVTLAIAGVALSLSRKLS

Extracellular domain of EndoBI-1
                                       SEQ ID NO: 4
NADAVSPTQETIQSTGRHEMVYYRAWRDVTMKGVNTDLPDDNWISMYDIP

YGVDVVNIFSYVPSGQEEQAQPFYDKLKSDYAPYLHSRGIKLVRGIDYTG

VAVNGFRTFMKEQNKTESEATEADYDAYAKQVIDKYMISVGLDGLDIDME

AHPNDADVKISDNVIRALSKHIGPKSAKPDTTMELYDINGSYLNPFKNVA

ECFDYVAYQQYGSSSDRTARAAADYQPYIGNEFVPGLTFPEEGDMNNRWY

DATEPYEESHFYQVASYVREHNLGGMFVYALDRDGRNYDEDLRRIVPSNL
```

-continued

LWTKTAIAESEGMALDTAKTAANHYLDRMSLRQVIDDNAASADKARDMVG

KAANLYETNKAVLGGDYGEGFSNTYDPTLEAGLLGIDISVLQQQIDKSSE

IIGADTAESDAKTALRMARDAAIDGLTGKIYTADQVSAWSQALKAALDAT

VPVPTPDSTDQNGNRDKVTNHKVQGQPKQLSAT

Extracellular domain of EndoBI-2 (BLIF_1310 from *B. infantis* SC142)
SEQ ID NO: 5

VANAQEGDSPVAASQEGNGNKHFMVYYRAWRDVTMKGVNTDLPDDNWISM

YDIPYGIDVVNVFSYVPSGQEAAAQPFYDKLKSDYAPYLHARGVKLVRGL

DYSGVMVDGFKTWIAQQGKNVDSATESDYDAYADHVIETYMTSVGLDGLD

IDMETFPDAAQVAISDQVITALAKRIGPKSDNPEGTMFLYDTNGSYTAPF

KNVSDCFDYVAYQQYGSDSNRTAKAAATYEQFIDSTKFVPGLTFPEEGDM

NNRWNDATEPYLDSHFYDVASYSYDHNLGGMFVYALDRDGRTYSDDDLAH

IKPSNLIWTKTAIAQSQGMSLENAKQAANHFLDRMSYTKDVPAETRQTVA

AATNLYEVNKAVLGADWNDGYSNTYDPTLELSLASIDTTALTGAIAKADA

LLADGATDTDVRTTLTTARNAA

Extracellular domain of EndoBB (BLD_0197 from *B. longum* DJO10A)
SEQ ID NO: 6

CSGGTSATKYTITPENENEELVLGNRPEASYWFPEDLLKWNADKDPNLAY

NVSTVPLAKRVDKADLKPVNDTQNTDTKVMAISIMNSSTSGNAPHGLNTA

NANTFSYWQYVDELVYWGGSSGEGIIVPPSPDVTDMGHTNGVPVLGTVFF

PQNVSGGKVEWLDQTLAQKSDGSFPVADKLIEVATTYGEDGWFINQETEG

ENETSLGADYATKMQAFIAYLKKQAPDLRVVYYDSMTKDGSIDWQNALTD

ENSMYMTDGDHPIADEMELNEWWTEDKLAGDDLLAASATKAKELGIDPYS

LYAGIDVQADGYDTPVKWNLFAGKDGKTHTSLGLYCPSWAYWSAGNPTTF

RKNESRLWVNDEGNPSVSTPYEDDEKWTGVSNYVAEQSAVTSLPFVTNEN

NGSGYSFFREGKQISKMDWNNRSVSDIQPTYRWIVADEGGNKTKADYSDA

DAWYGGSSLKFSGKVAKDGKTMVKLYSASVKTGAKPTLSIAAKANVDTDL

KAVLTFADGSVETVNGKKKVGNDWGVIDYDIAKLSNKTLTGIDFTYQSSE

DKTGYELLLGNITLKDGSEETELGKVTEVKVDDSEFDDDALYAGARISWK

TDGKAPAYEIYQINEDKSRSFLGVSNVENFYANALTRVGETNNTTFEIVP

VDRYGTQGTSAKADMDWPDNSKPKAGATASRTLLNVGDEVTFTSASSKNT

AEVAWSLPGSSKEHATGKSVTVTYDKEGVYDVEITAKNKSGEATATLKGQ

IVVSADVMDLVLLSQGAQVSADGFTNGNEKPEFAVDGDVKTKWCVTGPAP

HELVVDLGAPKTVSQVDISHAQAGGEDASMNTQEYAIEVSEDGTEYTQVA

LVKGNTEGATSNAFAPVNARYVKLVVNKPTQGSDTAARIYEMQVRGADGA

IL

What is claimed is:

1. A method of deglycosylating a glycoprotein comprising a high mannose, complex, or hybrid N-glycan, the method comprising
contacting the glycoprotein with a polypeptide comprising a sequence at least 90% identical to SEQ ID NO:4, wherein the polypeptide lacks a transmembrane domain, thereby deglycosylating the glycoprotein and generating deglycosylated protein and free glycans.

2. The method of claim 1, wherein the glycoprotein comprises a high mannose N-glycan.

3. The method of claim 1, wherein the glycoprotein comprises a complex N-glycan.

4. The method of claim 1, wherein the glycoprotein comprises a hybrid N-glycan.

5. A composition comprising:
(i) a recombinant polypeptide comprising a sequence at least 90% identical to SEQ ID NO:4 wherein said polypeptide can cleave high mannose, complex, and hybrid N-glycans from a glycoprotein and wherein the polypeptide lacks a transmembrane domain; and
(ii) a glycoprotein, wherein the glycoprotein comprises a high mannose, complex, or hybrid N-glycan.

6. The composition of claim 5, wherein the glycoprotein is selected from the group consisting of: lactoferrin, whey, and immunoglobulin.

7. The composition of claim 5, wherein the N-glycan comprises core fucosylation, terminal fucosylation, or terminal sialylation.

8. The composition of claim 5, wherein the polypeptide is a transmembrane protein in a cell membrane protein in a cell.

9. The composition of claim 5, wherein the glycoprotein comprises a high mannose N-glycan.

10. The composition of claim 5, wherein the glycoprotein comprises a complex N-glycan.

11. The composition of claim 5, wherein the glycoprotein comprises a hybrid N-glycan.

* * * * *

SEQUENCE LISTING

```
<160> NUMBER OF SEQ ID NOS: 82

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 1

Gly Leu Asp Ile Asp Met Glu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Phe Ile Asn Gln Glu Thr
1               5

<210> SEQ ID NO 3
<211> LENGTH: 545
<212> TYPE: PRT
<213> ORGANISM: Bifidobacterium infantis

<400> SEQUENCE: 3

Met Thr Phe Ile Lys Gln Met Met Pro Arg Tyr Val Ala Ser Met Thr
1               5                   10                  15

Ala Gly Ile Val Ala Ala Ala Met Ala Ala Thr Cys Ala Phe Ala Pro
```

-continued

```
                20                  25                  30
Val Ala Asn Ala Asp Ala Val Ser Pro Thr Gln Glu Thr Ile Gln Ser
            35                  40                  45
Thr Gly Arg His Phe Met Val Tyr Tyr Arg Ala Trp Arg Asp Val Thr
        50                  55                  60
Met Lys Gly Val Asn Thr Asp Leu Pro Asp Asn Trp Ile Ser Met
65                      70                  75                  80
Tyr Asp Ile Pro Tyr Gly Val Asp Val Asn Ile Phe Ser Tyr Val
                    85                  90                  95
Pro Ser Gly Gln Glu Gln Ala Gln Pro Phe Tyr Asp Lys Leu Lys
                100                 105                 110
Ser Asp Tyr Ala Pro Tyr Leu His Ser Arg Gly Ile Lys Leu Val Arg
            115                 120                 125
Gly Ile Asp Tyr Thr Gly Val Ala Val Asn Gly Phe Arg Thr Phe Met
        130                 135                 140
Lys Glu Gln Asn Lys Thr Glu Ser Glu Ala Thr Glu Ala Asp Tyr Asp
145                     150                 155                 160
Ala Tyr Ala Lys Gln Val Ile Asp Lys Tyr Met Ile Ser Val Gly Leu
                165                 170                 175
Asp Gly Leu Asp Ile Asp Met Glu Ala His Pro Asn Asp Ala Asp Val
            180                 185                 190
Lys Ile Ser Asp Asn Val Ile Arg Ala Leu Ser Lys His Ile Gly Pro
        195                 200                 205
Lys Ser Ala Lys Pro Asp Thr Thr Met Phe Leu Tyr Asp Thr Asn Gly
        210                 215                 220
Ser Tyr Leu Asn Pro Phe Lys Asn Val Ala Glu Cys Phe Asp Tyr Val
225                 230                 235                 240
Ala Tyr Gln Gln Tyr Gly Ser Ser Asp Arg Thr Ala Arg Ala Ala
                245                 250                 255
Ala Asp Tyr Gln Pro Tyr Ile Gly Asn Glu Phe Val Pro Gly Leu Thr
            260                 265                 270
Phe Pro Glu Glu Gly Asp Met Asn Asn Arg Trp Tyr Asp Ala Thr Glu
        275                 280                 285
Pro Tyr Glu Glu Ser His Phe Tyr Gln Val Ala Ser Tyr Val Arg Glu
        290                 295                 300
His Asn Leu Gly Gly Met Phe Val Tyr Ala Leu Asp Arg Asp Gly Arg
305                 310                 315                 320
Asn Tyr Asp Glu Asp Leu Arg Arg Ile Val Pro Ser Asn Leu Leu Trp
                325                 330                 335
Thr Lys Thr Ala Ile Ala Glu Ser Glu Gly Met Ala Leu Asp Thr Ala
            340                 345                 350
Lys Thr Ala Ala Asn His Tyr Leu Asp Arg Met Ser Leu Arg Gln Val
        355                 360                 365
Ile Asp Asp Asn Ala Ala Ser Ala Asp Lys Ala Arg Asp Met Val Gly
        370                 375                 380
Lys Ala Ala Asn Leu Tyr Glu Thr Asn Lys Ala Val Leu Gly Gly Asp
385                 390                 395                 400
Tyr Gly Glu Gly Phe Ser Asn Thr Tyr Asp Pro Thr Leu Glu Ala Gly
                405                 410                 415
Leu Leu Gly Ile Asp Ile Ser Val Leu Gln Gln Gln Ile Asp Lys Ser
            420                 425                 430
Ser Glu Ile Ile Gly Ala Asp Thr Ala Glu Ser Asp Ala Lys Thr Ala
        435                 440                 445
```

```
Leu Arg Met Ala Arg Asp Ala Ile Asp Gly Leu Thr Gly Lys Ile
    450                 455                 460

Tyr Thr Ala Asp Gln Val Ser Ala Trp Ser Gln Ala Leu Lys Ala Ala
465                 470                 475                 480

Leu Asp Ala Thr Val Pro Val Pro Thr Pro Asp Ser Thr Asp Gln Asn
                485                 490                 495

Gly Asn Arg Asp Lys Val Thr Asn His Lys Val Gln Gly Gln Pro Lys
            500                 505                 510

Gln Leu Ser Ala Thr Gly Ile Ser Thr Asp Ile Ile Val Ala Val Gly
        515                 520                 525

Val Thr Leu Ala Ile Ala Gly Val Ala Leu Ser Leu Ser Arg Lys Leu
    530                 535                 540

Ser
545

<210> SEQ ID NO 4
<211> LENGTH: 483
<212> TYPE: PRT
<213> ORGANISM: Bifidobacterium infantis

<400> SEQUENCE: 4

Asn Ala Asp Ala Val Ser Pro Thr Gln Glu Thr Ile Gln Ser Thr Gly
1               5                   10                  15

Arg His Phe Met Val Tyr Tyr Arg Ala Trp Arg Asp Val Thr Met Lys
            20                  25                  30

Gly Val Asn Thr Asp Leu Pro Asp Asp Asn Trp Ile Ser Met Tyr Asp
        35                  40                  45

Ile Pro Tyr Gly Val Asp Val Asn Ile Phe Ser Tyr Val Pro Ser
    50                  55                  60

Gly Gln Glu Glu Gln Ala Gln Pro Phe Tyr Asp Lys Leu Lys Ser Asp
65              70                  75                  80

Tyr Ala Pro Tyr Leu His Ser Arg Gly Ile Lys Leu Val Arg Gly Ile
                85                  90                  95

Asp Tyr Thr Gly Val Ala Val Asn Gly Phe Arg Thr Phe Met Lys Glu
            100                 105                 110

Gln Asn Lys Thr Glu Ser Glu Ala Thr Glu Ala Asp Tyr Asp Ala Tyr
        115                 120                 125

Ala Lys Gln Val Ile Asp Lys Tyr Met Ile Ser Val Gly Leu Asp Gly
    130                 135                 140

Leu Asp Ile Asp Met Glu Ala His Pro Asn Asp Ala Asp Val Lys Ile
145                 150                 155                 160

Ser Asp Asn Val Ile Arg Ala Leu Ser Lys His Ile Gly Pro Lys Ser
                165                 170                 175

Ala Lys Pro Asp Thr Thr Met Phe Leu Tyr Asp Thr Asn Gly Ser Tyr
            180                 185                 190

Leu Asn Pro Phe Lys Asn Val Ala Glu Cys Phe Asp Tyr Val Ala Tyr
        195                 200                 205

Gln Gln Tyr Gly Ser Ser Ser Asp Arg Thr Ala Arg Ala Ala Ala Asp
    210                 215                 220

Tyr Gln Pro Tyr Ile Gly Asn Glu Phe Val Pro Gly Leu Thr Phe Pro
225                 230                 235                 240

Glu Glu Gly Asp Met Asn Asn Arg Trp Tyr Asp Ala Thr Glu Pro Tyr
                245                 250                 255

Glu Glu Ser His Phe Tyr Gln Val Ala Ser Tyr Val Arg Glu His Asn
```

```
            260                 265                 270
Leu Gly Gly Met Phe Val Tyr Ala Leu Asp Arg Asp Gly Arg Asn Tyr
            275                 280                 285

Asp Glu Asp Leu Arg Arg Ile Val Pro Ser Asn Leu Leu Trp Thr Lys
        290                 295                 300

Thr Ala Ile Ala Glu Ser Glu Gly Met Ala Leu Asp Thr Ala Lys Thr
305                 310                 315                 320

Ala Ala Asn His Tyr Leu Asp Arg Met Ser Leu Arg Gln Val Ile Asp
                325                 330                 335

Asp Asn Ala Ala Ser Ala Asp Lys Ala Arg Asp Met Val Gly Lys Ala
            340                 345                 350

Ala Asn Leu Tyr Glu Thr Asn Lys Ala Val Leu Gly Gly Asp Tyr Gly
        355                 360                 365

Glu Gly Phe Ser Asn Thr Tyr Asp Pro Thr Leu Glu Ala Gly Leu Leu
    370                 375                 380

Gly Ile Asp Ile Ser Val Leu Gln Gln Gln Ile Asp Lys Ser Ser Glu
385                 390                 395                 400

Ile Ile Gly Ala Asp Thr Ala Glu Ser Asp Ala Lys Thr Ala Leu Arg
                405                 410                 415

Met Ala Arg Asp Ala Ala Ile Asp Gly Leu Thr Gly Lys Ile Tyr Thr
            420                 425                 430

Ala Asp Gln Val Ser Ala Trp Ser Gln Ala Leu Lys Ala Ala Leu Asp
        435                 440                 445

Ala Thr Val Pro Val Pro Thr Pro Asp Ser Thr Asp Gln Asn Gly Asn
    450                 455                 460

Arg Asp Lys Val Thr Asn His Lys Val Gln Gly Gln Pro Lys Gln Leu
465                 470                 475                 480

Ser Ala Thr

<210> SEQ ID NO 5
<211> LENGTH: 422
<212> TYPE: PRT
<213> ORGANISM: Bifidobacterium infantis

<400> SEQUENCE: 5

Val Ala Asn Ala Gln Glu Gly Asp Ser Pro Val Ala Ala Ser Gln Glu
1               5                   10                  15

Gly Asn Gly Asn Lys His Phe Met Val Tyr Tyr Arg Ala Trp Arg Asp
            20                  25                  30

Val Thr Met Lys Gly Val Asn Thr Asp Leu Pro Asp Asp Asn Trp Ile
        35                  40                  45

Ser Met Tyr Asp Ile Pro Tyr Gly Ile Asp Val Asn Val Phe Ser
50                  55                  60

Tyr Val Pro Ser Gly Gln Glu Ala Ala Gln Pro Phe Tyr Asp Lys
65                  70                  75              80

Leu Lys Ser Asp Tyr Ala Pro Tyr Leu His Ala Arg Gly Val Lys Leu
                85                  90                  95

Val Arg Gly Leu Asp Tyr Ser Gly Val Met Val Asp Gly Phe Lys Thr
            100                 105                 110

Trp Ile Ala Gln Gln Gly Lys Asn Val Asp Ser Ala Thr Glu Ser Asp
        115                 120                 125

Tyr Asp Ala Tyr Ala Asp His Val Ile Glu Thr Tyr Met Thr Ser Val
    130                 135                 140

Gly Leu Asp Gly Leu Asp Ile Asp Met Glu Thr Phe Pro Asp Ala Ala
```

```
                145                 150                 155                 160
        Gln Val Ala Ile Ser Asp Gln Val Ile Thr Ala Leu Ala Lys Arg Ile
                        165                 170                 175
        Gly Pro Lys Ser Asp Asn Pro Glu Gly Thr Met Phe Leu Tyr Asp Thr
                        180                 185                 190
        Asn Gly Ser Tyr Thr Ala Pro Phe Lys Asn Val Ser Asp Cys Phe Asp
                        195                 200                 205
        Tyr Val Ala Tyr Gln Gln Tyr Gly Ser Asp Ser Asn Arg Thr Ala Lys
                    210                 215                 220
        Ala Ala Ala Thr Tyr Glu Gln Phe Ile Asp Ser Thr Lys Phe Val Pro
        225                 230                 235                 240
        Gly Leu Thr Phe Pro Glu Gly Asp Met Asn Asn Arg Trp Asn Asp
                            245                 250                 255
        Ala Thr Glu Pro Tyr Leu Asp Ser His Phe Tyr Asp Val Ala Ser Tyr
                        260                 265                 270
        Ser Tyr Asp His Asn Leu Gly Gly Met Phe Val Tyr Ala Leu Asp Arg
                    275                 280                 285
        Asp Gly Arg Thr Tyr Ser Asp Asp Leu Ala His Ile Lys Pro Ser
                290                 295                 300
        Asn Leu Ile Trp Thr Lys Thr Ala Ile Ala Gln Ser Gln Gly Met Ser
        305                 310                 315                 320
        Leu Glu Asn Ala Lys Gln Ala Ala Asn His Phe Leu Asp Arg Met Ser
                        325                 330                 335
        Tyr Thr Lys Asp Val Pro Ala Glu Thr Arg Gln Thr Val Ala Ala Ala
                        340                 345                 350
        Thr Asn Leu Tyr Glu Val Asn Lys Ala Val Leu Gly Ala Asp Trp Asn
                    355                 360                 365
        Asp Gly Tyr Ser Asn Thr Tyr Asp Pro Thr Leu Glu Leu Ser Leu Ala
                370                 375                 380
        Ser Ile Asp Thr Thr Ala Leu Thr Gly Ala Ile Ala Lys Ala Asp Ala
        385                 390                 395                 400
        Leu Leu Ala Asp Gly Ala Thr Asp Thr Asp Val Arg Thr Thr Leu Thr
                        405                 410                 415
        Thr Ala Arg Asn Ala Ala
                        420

<210> SEQ ID NO 6
<211> LENGTH: 902
<212> TYPE: PRT
<213> ORGANISM: Bifidobacterium longum

<400> SEQUENCE: 6

Cys Ser Gly Gly Thr Ser Ala Thr Lys Tyr Thr Ile Thr Pro Glu Asn
        1               5                   10                  15
        Glu Asn Glu Glu Leu Val Leu Gly Asn Arg Pro Glu Ala Ser Tyr Trp
                        20                  25                  30
        Phe Pro Glu Asp Leu Leu Lys Trp Asn Ala Asp Lys Pro Asn Leu
                    35                  40                  45
        Ala Tyr Asn Val Ser Thr Val Pro Leu Ala Lys Arg Val Asp Lys Ala
            50                  55                  60
        Asp Leu Lys Pro Val Asn Asp Thr Gln Asn Thr Asp Thr Lys Val Met
        65                  70                  75                  80
        Ala Ile Ser Ile Met Asn Ser Ser Thr Ser Gly Asn Ala Pro His Gly
                        85                  90                  95
```

```
Leu Asn Thr Ala Asn Ala Asn Thr Phe Ser Tyr Trp Gln Tyr Val Asp
                100                 105                 110

Glu Leu Val Tyr Trp Gly Gly Ser Ser Gly Glu Gly Ile Ile Val Pro
            115                 120                 125

Pro Ser Pro Asp Val Thr Asp Met Gly His Thr Asn Gly Val Pro Val
        130                 135                 140

Leu Gly Thr Val Phe Phe Pro Gln Asn Val Ser Gly Gly Lys Val Glu
145                 150                 155                 160

Trp Leu Asp Gln Thr Leu Ala Gln Lys Ser Asp Gly Ser Phe Pro Val
                165                 170                 175

Ala Asp Lys Leu Ile Glu Val Ala Thr Thr Tyr Gly Phe Asp Gly Trp
            180                 185                 190

Phe Ile Asn Gln Glu Thr Glu Gly Glu Asn Glu Thr Ser Leu Gly Ala
        195                 200                 205

Asp Tyr Ala Thr Lys Met Gln Ala Phe Ile Ala Tyr Leu Lys Lys Gln
        210                 215                 220

Ala Pro Asp Leu Arg Val Val Tyr Tyr Asp Ser Met Thr Lys Asp Gly
225                 230                 235                 240

Ser Ile Asp Trp Gln Asn Ala Leu Thr Asp Glu Asn Ser Met Tyr Met
                245                 250                 255

Thr Asp Gly Asp His Pro Ile Ala Asp Glu Met Phe Leu Asn Phe Trp
                260                 265                 270

Trp Thr Glu Asp Lys Leu Ala Gly Asp Asp Leu Leu Ala Ser Ala
            275                 280                 285

Thr Lys Ala Lys Glu Leu Gly Ile Asp Pro Tyr Ser Leu Tyr Ala Gly
            290                 295                 300

Ile Asp Val Gln Ala Asp Gly Tyr Asp Thr Pro Val Lys Trp Asn Leu
305                 310                 315                 320

Phe Ala Gly Lys Asp Gly Lys Thr His Thr Ser Leu Gly Leu Tyr Cys
                325                 330                 335

Pro Ser Trp Ala Tyr Trp Ser Ala Gly Asn Pro Thr Thr Phe Arg Lys
            340                 345                 350

Asn Glu Ser Arg Leu Trp Val Asn Asp Glu Gly Asn Pro Ser Val Ser
        355                 360                 365

Thr Pro Tyr Glu Asp Asp Glu Lys Trp Thr Gly Val Ser Asn Tyr Val
    370                 375                 380

Ala Glu Gln Ser Ala Val Thr Ser Leu Pro Phe Val Thr Asn Phe Asn
385                 390                 395                 400

Asn Gly Ser Gly Tyr Ser Phe Phe Arg Glu Gly Lys Gln Ile Ser Lys
                405                 410                 415

Met Asp Trp Asn Asn Arg Ser Val Ser Asp Ile Gln Pro Thr Tyr Arg
            420                 425                 430

Trp Ile Val Ala Asp Glu Gly Gly Asn Lys Thr Lys Ala Asp Tyr Ser
        435                 440                 445

Asp Ala Asp Ala Trp Tyr Gly Gly Ser Ser Leu Lys Phe Ser Gly Lys
        450                 455                 460

Val Ala Lys Asp Gly Lys Thr Met Val Lys Leu Tyr Ser Ala Ser Val
465                 470                 475                 480

Lys Thr Gly Ala Lys Pro Thr Leu Ser Ile Ala Ala Lys Ala Asn Val
                485                 490                 495

Asp Thr Asp Leu Lys Ala Val Leu Thr Phe Ala Asp Gly Ser Val Glu
            500                 505                 510

Thr Val Asn Gly Lys Lys Lys Val Gly Asn Asp Trp Gly Val Ile Asp
```

```
            515                 520                 525
Tyr Asp Ile Ala Lys Leu Ser Asn Lys Thr Leu Thr Gly Ile Asp Phe
            530                 535                 540

Thr Tyr Gln Ser Ser Glu Asp Lys Thr Gly Tyr Glu Leu Leu Leu Gly
545                 550                 555                 560

Asn Ile Thr Leu Lys Asp Gly Ser Glu Glu Thr Glu Leu Gly Lys Val
                565                 570                 575

Thr Glu Val Lys Val Asp Asp Ser Glu Phe Asp Asp Ala Leu Tyr
            580                 585                 590

Ala Gly Ala Arg Ile Ser Trp Lys Thr Asp Gly Lys Ala Pro Ala Tyr
            595                 600                 605

Glu Ile Tyr Gln Ile Asn Glu Asp Lys Ser Arg Ser Phe Leu Gly Val
            610                 615                 620

Ser Asn Val Glu Asn Phe Tyr Ala Asn Ala Leu Thr Arg Val Gly Glu
625                 630                 635                 640

Thr Asn Asn Thr Thr Phe Glu Ile Val Pro Val Asp Arg Tyr Gly Thr
                645                 650                 655

Gln Gly Thr Ser Ala Lys Ala Asp Met Asp Trp Pro Asp Asn Ser Lys
            660                 665                 670

Pro Lys Ala Gly Ala Thr Ala Ser Arg Thr Leu Leu Asn Val Gly Asp
            675                 680                 685

Glu Val Thr Phe Thr Ser Ala Ser Ser Lys Asn Thr Ala Glu Val Ala
            690                 695                 700

Trp Ser Leu Pro Gly Ser Ser Lys Glu His Ala Thr Gly Lys Ser Val
705                 710                 715                 720

Thr Val Thr Tyr Asp Lys Glu Gly Val Tyr Asp Val Glu Ile Thr Ala
                725                 730                 735

Lys Asn Lys Ser Gly Glu Ala Thr Ala Thr Leu Lys Gly Gln Ile Val
                740                 745                 750

Val Ser Ala Asp Val Met Asp Leu Val Leu Ser Gln Gly Ala Gln
            755                 760                 765

Val Ser Ala Asp Gly Phe Thr Asn Gly Asn Glu Lys Pro Glu Phe Ala
            770                 775                 780

Val Asp Gly Asp Val Lys Thr Lys Trp Cys Val Thr Gly Pro Ala Pro
785                 790                 795                 800

His Glu Leu Val Val Asp Leu Gly Ala Pro Lys Thr Val Ser Gln Val
                805                 810                 815

Asp Ile Ser His Ala Gln Ala Gly Gly Glu Asp Ala Ser Met Asn Thr
            820                 825                 830

Gln Glu Tyr Ala Ile Glu Val Ser Glu Asp Gly Thr Glu Tyr Thr Gln
            835                 840                 845

Val Ala Leu Val Lys Gly Asn Thr Glu Gly Ala Thr Ser Asn Ala Phe
            850                 855                 860

Ala Pro Val Asn Ala Arg Tyr Val Lys Leu Val Val Asn Lys Pro Thr
865                 870                 875                 880

Gln Gly Ser Asp Thr Ala Ala Arg Ile Tyr Glu Met Gln Val Arg Gly
            885                 890                 895

Ala Asp Gly Ala Ile Leu
            900

<210> SEQ ID NO 7
<211> LENGTH: 50
<212> TYPE: PRT
<213> ORGANISM: Bifidobacterium infantis
```

-continued

<400> SEQUENCE: 7

```
Thr Glu Ser Glu Ala Thr Glu Ala Asp Tyr Asp Ala Tyr Ala Lys Gln
1               5                   10                  15
Val Ile Asp Lys Tyr Met Ile Ser Val Gly Leu Asp Gly Leu Asp Ile
            20                  25                  30
Asp Met Glu Ala His Pro Asn Asp Ala Asp Val Lys Ile Ser Asp Asn
        35                  40                  45
Val Ile
    50
```

<210> SEQ ID NO 8
<211> LENGTH: 50
<212> TYPE: PRT
<213> ORGANISM: Bifidobacterium infantis

<400> SEQUENCE: 8

```
Thr Glu Ser Glu Ala Thr Glu Ala Asp Tyr Asp Ala Tyr Ala Lys Gln
1               5                   10                  15
Val Ile Asp Lys Tyr Met Ile Ser Val Gly Leu Asp Gly Leu Asp Ile
            20                  25                  30
Asp Met Glu Ala His Pro Asn Asp Ala Asp Val Lys Ile Ser Asp Asn
        35                  40                  45
Val Ile
    50
```

<210> SEQ ID NO 9
<211> LENGTH: 50
<212> TYPE: PRT
<213> ORGANISM: Bifidobacterium infantis

<400> SEQUENCE: 9

```
Thr Glu Ser Glu Ala Thr Glu Ala Asp Tyr Asp Ala Tyr Ala Lys Gln
1               5                   10                  15
Val Ile Asp Lys Tyr Met Ile Ser Val Gly Leu Asp Gly Leu Asp Ile
            20                  25                  30
Asp Met Glu Ala His Pro Asn Asp Ala Asp Val Lys Ile Ser Asp Asn
        35                  40                  45
Val Ile
    50
```

<210> SEQ ID NO 10
<211> LENGTH: 50
<212> TYPE: PRT
<213> ORGANISM: Bifidobacterium infantis

<400> SEQUENCE: 10

```
Thr Glu Ser Glu Ala Thr Glu Ala Asp Tyr Asp Ala Tyr Ala Lys Gln
1               5                   10                  15
Val Ile Asp Lys Tyr Met Ile Ser Val Gly Leu Asp Gly Leu Asp Ile
            20                  25                  30
Asp Met Glu Ala His Pro Asn Asp Ala Asp Val Lys Ile Ser Asp Asn
        35                  40                  45
Val Ile
    50
```

<210> SEQ ID NO 11
<211> LENGTH: 50
<212> TYPE: PRT

<213> ORGANISM: Bifidobacterium infantis

<400> SEQUENCE: 11

Thr Glu Ser Glu Ala Thr Glu Ala Asp Tyr Asp Ala Tyr Ala Lys Gln
1               5                   10                  15

Val Ile Asp Lys Tyr Met Ile Ser Val Gly Leu Asp Gly Leu Asp Ile
            20                  25                  30

Asp Met Glu Ala His Pro Asn Asp Ala Asp Val Lys Ile Ser Asp Asn
        35                  40                  45

Val Ile
    50

<210> SEQ ID NO 12
<211> LENGTH: 50
<212> TYPE: PRT
<213> ORGANISM: Bifidobacterium infantis

<400> SEQUENCE: 12

Thr Glu Ser Glu Ala Thr Glu Ala Asp Tyr Asp Ala Tyr Ala Lys Gln
1               5                   10                  15

Val Ile Asp Lys Tyr Met Ile Ser Val Gly Leu Asp Gly Leu Asp Ile
            20                  25                  30

Asp Met Glu Ala His Pro Asn Asp Ala Asp Val Lys Ile Ser Asp Asn
        35                  40                  45

Val Ile
    50

<210> SEQ ID NO 13
<211> LENGTH: 50
<212> TYPE: PRT
<213> ORGANISM: Bifidobacterium infantis

<400> SEQUENCE: 13

Thr Glu Ser Glu Ala Thr Glu Ala Asp Tyr Asp Ala Tyr Ala Lys Gln
1               5                   10                  15

Val Ile Asp Lys Tyr Met Ile Ser Val Gly Leu Asp Gly Leu Asp Ile
            20                  25                  30

Asp Met Glu Ala His Pro Asn Asp Ala Asp Val Lys Ile Ser Asp Asn
        35                  40                  45

Val Ile
    50

<210> SEQ ID NO 14
<211> LENGTH: 50
<212> TYPE: PRT
<213> ORGANISM: Bifidobacterium infantis

<400> SEQUENCE: 14

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 15
<211> LENGTH: 50

```
<212> TYPE: PRT
<213> ORGANISM: Bifidobacterium infantis

<400> SEQUENCE: 15

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 16
<211> LENGTH: 50
<212> TYPE: PRT
<213> ORGANISM: Bifidobacterium infantis

<400> SEQUENCE: 16

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 17
<211> LENGTH: 50
<212> TYPE: PRT
<213> ORGANISM: Bifidobacterium longum

<400> SEQUENCE: 17

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 18
<211> LENGTH: 50
<212> TYPE: PRT
<213> ORGANISM: Bifidobacterium longum

<400> SEQUENCE: 18

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 19
```

```
<211> LENGTH: 50
<212> TYPE: PRT
<213> ORGANISM: Bifidobacterium longum

<400> SEQUENCE: 19

Asn Val Asp Ser Ala Thr Glu Ser Asp Tyr Asp Ala Tyr Ala Asp His
1               5                   10                  15

Val Ile Glu Thr Tyr Met Thr Ser Val Gly Leu Asp Gly Leu Asp Ile
            20                  25                  30

Asp Met Glu Thr Phe Pro Asp Ala Ala Gln Val Ala Ile Ser Asp Gln
        35                  40                  45

Val Ile
    50

<210> SEQ ID NO 20
<211> LENGTH: 50
<212> TYPE: PRT
<213> ORGANISM: Enterococcus faecalis

<400> SEQUENCE: 20

Ala Gly Thr Thr Pro Thr Glu Ala Glu Phe Asp Ala Tyr Ala Lys Glu
1               5                   10                  15

Leu Leu Thr Lys Phe Val Asp Asp Leu Gly Ile Asp Gly Leu Asp Ile
            20                  25                  30

Asp Met Glu Thr Arg Pro Ser Glu Lys Asp Ile Val Leu Ser Asn Gly
        35                  40                  45

Val Ile
    50

<210> SEQ ID NO 21
<211> LENGTH: 54
<212> TYPE: PRT
<213> ORGANISM: Bifidobacterium breve

<400> SEQUENCE: 21

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50

<210> SEQ ID NO 22
<211> LENGTH: 54
<212> TYPE: PRT
<213> ORGANISM: Bifidobacterium breve

<400> SEQUENCE: 22

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50
```

```
<210> SEQ ID NO 23
<211> LENGTH: 54
<212> TYPE: PRT
<213> ORGANISM: Bifidobacterium breve

<400> SEQUENCE: 23

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50

<210> SEQ ID NO 24
<211> LENGTH: 54
<212> TYPE: PRT
<213> ORGANISM: Bifidobacterium breve

<400> SEQUENCE: 24

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50

<210> SEQ ID NO 25
<211> LENGTH: 54
<212> TYPE: PRT
<213> ORGANISM: Bifidobacterium breve

<400> SEQUENCE: 25

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50

<210> SEQ ID NO 26
<211> LENGTH: 54
<212> TYPE: PRT
<213> ORGANISM: Bifidobacterium breve

<400> SEQUENCE: 26

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
    50
```

<210> SEQ ID NO 27
<211> LENGTH: 54
<212> TYPE: PRT
<213> ORGANISM: Bifidobacterium breve

<400> SEQUENCE: 27

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
        50

<210> SEQ ID NO 28
<211> LENGTH: 54
<212> TYPE: PRT
<213> ORGANISM: Bifidobacterium breve

<400> SEQUENCE: 28

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
        50

<210> SEQ ID NO 29
<211> LENGTH: 54
<212> TYPE: PRT
<213> ORGANISM: Bifidobacterium longum

<400> SEQUENCE: 29

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
        50

<210> SEQ ID NO 30
<211> LENGTH: 54
<212> TYPE: PRT
<213> ORGANISM: Bifidobacterium breve

<400> SEQUENCE: 30

Ser Asp Gly Ser Phe Pro Val Ala Asp Lys Leu Ile Glu Val Ala Thr
1               5                   10                  15

Thr Tyr Gly Phe Asp Gly Trp Phe Ile Asn Gln Glu Thr Glu Gly Glu
            20                  25                  30

Asn Glu Thr Ser Leu Gly Ala Asp Tyr Ala Thr Lys Met Gln Ala Phe
        35                  40                  45

Ile Ala Tyr Leu Lys Lys
        50

<210> SEQ ID NO 31
<211> LENGTH: 50
<212> TYPE: PRT
<213> ORGANISM: Streptococcus pneumoniae

<400> SEQUENCE: 31

Ala Asp Gly Ser Phe Pro Ile Ala Arg Lys Leu Val Asp Met Ala Lys
1               5                   10                  15

Tyr Tyr Gly Tyr Asp Gly Tyr Phe Ile Asn Gln Glu Thr Thr Gly Asp
            20                  25                  30

Leu Val Lys Pro Leu Gly Glu Lys Met Arg Gln Phe Met Leu Tyr Ser
        35                  40                  45

Lys Glu
    50

<210> SEQ ID NO 32
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: n is a, c, g, or t

<400> SEQUENCE: 32
taytggcart aygtngay                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 33
ccayttytcr tcrtcytc                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: n is a, c, g, or t

<400> SEQUENCE: 34
ctngayathg ayatggar                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)

<223> OTHER INFORMATION: n is a, c, g, or t

<400> SEQUENCE: 35
nganccrtay tgytgrta                                            18

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
caaccgaggt catgtacgtt                                          20

<210> SEQ ID NO 37
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 37
cgtaatcgct cttgagcttg tc                                       22

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
actgggaacg tagctgaaca                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
aacgtacatg acctcggttg                                          20

<210> SEQ ID NO 40
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 40
cacgatgttc ctttacgaca cc                                       22

<210> SEQ ID NO 41
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 41
gacaccaatg gcagctacac tg                                       22

<210> SEQ ID NO 42
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 42
caccatgaat gcggacgccg tttctccgac                                      30

<210> SEQ ID NO 43
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 43
gccggtcgca ctcagttgct tcgg                                            24

<210> SEQ ID NO 44
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 44
caccatggtt gcgaacgccc aggaggggga                                      30

<210> SEQ ID NO 45
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 45
cgccgcgttt ctggccgtgg tca                                             23

<210> SEQ ID NO 46
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 46
caccatgacc aagtacacga tcacaccgga g                                    31

<210> SEQ ID NO 47
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 47
ggtacgtggc gcagacggcg cgatcctc                                        28

<210> SEQ ID NO 48
<211> LENGTH: 27
<212> TYPE: DNA
<213> ORGANISM: Artificial Sequence
<220> FEATURE:
<223> OTHER INFORMATION: Synthetic polynucleotide
<220> FEATURE:

```
<221> NAME/KEY: misc_feature
<222> LOCATION: (1)..(1)
<223> OTHER INFORMATION: Residue modified by phosphate at 5' end

<400> SEQUENCE: 48
gatatcgaca tgcaggcgca cccgaat                                          27

<210> SEQ ID NO 49
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 49
ttcaccgagg cgtacaaca                                                   19

<210> SEQ ID NO 50
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 50
cgcatccgtg accacatag                                                   19

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
acagagccac ccctgcgatg                                                  20

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
gccggttccg acgccagatt                                                  20

<210> SEQ ID NO 53
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 53
cacgatgctg gtgagtgc                                                    18

<210> SEQ ID NO 54
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 54
ccggaaccgg taagatcc                                                    18
```

<210> SEQ ID NO 55
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 55
acaaccgttt cagcaagacc                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 56
gagcagacgg ttgaagaagg                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 57
atgatcgccg tcacgatatt                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
gaacatcagc agggagaagc                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59
tccggtcggc attcacgcac                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
ggcaacggtc tcggcgttgt                                               20

<210> SEQ ID NO 61
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 61
tggtctgcgc acgctgaagg                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62
ggcacctcgg ccatcacacc                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 63
ggccacgtcg gcttcaacga                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 64
gaacgccagc agcacgaggt                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 65
tcgtttcccg cgtgaccacg                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 66
ccacgtagcc gggggtcaga                    20

<210> SEQ ID NO 67
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 67
atcgaagccg tgtggatt                      18

<210> SEQ ID NO 68
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 68
cctcgttgta ggcgtcgta                                                19

<210> SEQ ID NO 69
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 69
acagctcgcg gtggagtcct                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 70
tccagcggct tgcctttcgg                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 71
gcagcagcgt gtcaaaccgc                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 72
gccgggaacg cggaaaggtt                                               20

<210> SEQ ID NO 73
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 73
cctgttcaac caggatgagt c                                             21

<210> SEQ ID NO 74
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 74
ccgtccacga cgaagtag                                             18

<210> SEQ ID NO 75
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 75
atcacgctca ccctccc                                              17

<210> SEQ ID NO 76
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 76
acatcgtcga agcggagt                                             18

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 77
ggttcctgag gtcttcacca                                           20

<210> SEQ ID NO 78
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 78
gccgagcttc tcaaattca                                            19

<210> SEQ ID NO 79
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 79
tcaagaagct cgacccgttg                                           20

<210> SEQ ID NO 80
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 80
ttggcgtaga agccgtatgt                                           20

<210> SEQ ID NO 81
<211> LENGTH: 19

```
<212> TYPE: DNA
<213> ORGANISM: Artificial Sequence
<220> FEATURE:
<223> OTHER INFORMATION: Synthetic polynucleotide

<400> SEQUENCE: 81
aagccgatag gttctccct                                              19

<210> SEQ ID NO 82
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 82
tcgccttggt gtacttgtct                                             20
```